US008592752B2

(12) United States Patent
Gorenstein et al.

(10) Patent No.: US 8,592,752 B2
(45) Date of Patent: Nov. 26, 2013

(54) TECHNIQUES FOR PERFORMING RETENTION-TIME MATCHING OF PRECURSOR AND PRODUCT IONS AND FOR CONSTRUCTING PRECURSOR AND PRODUCT ION SPECTRA

(75) Inventors: Marc V. Gorenstein, Needham, MA (US); Martha Degen Stapels, Millis, MA (US); Scott Geromanos, Middleton, NJ (US); Jeffrey C. Silva, Beverly, MA (US); Guo-Zhong Li, Westborough, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 12/992,147

(22) PCT Filed: May 29, 2009

(86) PCT No.: PCT/US2009/045373
§ 371 (c)(1),
(2), (4) Date: Feb. 28, 2011

(87) PCT Pub. No.: WO2009/146345
PCT Pub. Date: Dec. 3, 2009

(65) Prior Publication Data
US 2011/0226941 A1    Sep. 22, 2011

Related U.S. Application Data

(60) Provisional application No. 61/056,871, filed on May 29, 2008.

(51) Int. Cl.
*H01J 49/26* (2006.01)
*H01J 49/00* (2006.01)

(52) U.S. Cl.
USPC ............................ 250/282; 250/281; 702/23

(58) Field of Classification Search
USPC ..................................... 250/281, 282; 702/23
See application file for complete search history.

(56) References Cited

U.S. PATENT DOCUMENTS 6,444,979 B1 * 9/2002 Watanabe ..................... 250/282
6,451,611 B1 * 9/2002 Simonsen et al. ............. 436/94
(Continued)

FOREIGN PATENT DOCUMENTS

| WO | WO 2005114930 A2 * | 12/2005 |
| WO | 2006133191 | 12/2006 |
| WO | WO 2006133191 A2 * | 12/2006 |

OTHER PUBLICATIONS

PCT International Search Report for Application No. PCT/US09/45373, dated Jul. 31, 2009.
(Continued)

*Primary Examiner* — David A Vanore
*Assistant Examiner* — Wyatt Stoffa
(74) *Attorney, Agent, or Firm* — Muirhead and Saturnelli, LLC

(57) ABSTRACT

Techniques are described for matching a precursor ion with one or more related product ions. Input data sets are obtained from a plurality of injections. Each of the input data sets includes a same precursor ion and one or more product ions. The input data sets are normalized in accordance with a single retention time for the precursor ion. For each input data set, it is determined which product ions are within a predetermined retention time window with respect to the single retention time for the precursor ion. If a product ion is within the predetermined retention time window in at least one of the input data sets, it is determined that the product ion is related to the precursor ion. An apparatus for analyzing a sample includes a chromatography module, a mass-spectrometry module, and a control unit.

24 Claims, 21 Drawing Sheets

(56) References Cited

U.S. PATENT DOCUMENTS

| | | |
|---|---|---|
| 7,595,485 B1 * | 9/2009 | Sadygov et al. .............. 250/282 |
| 7,982,180 B2 * | 7/2011 | Shilov et al. .................. 250/281 |
| 2003/0119062 A1 | 6/2003 | Brame |
| 2004/0014143 A1 | 1/2004 | Haskins et al. |
| 2004/0108452 A1 * | 6/2004 | Graber et al. ................. 250/281 |
| 2004/0195500 A1 | 10/2004 | Sachs et al. |
| 2005/0017163 A1 * | 1/2005 | Miller et al. .................. 250/281 |
| 2005/0092910 A1 * | 5/2005 | Geromanos et al. .......... 250/282 |
| 2005/0164324 A1 | 7/2005 | Gygi |
| 2005/0258355 A1 * | 11/2005 | Ogata et al. .................. 250/281 |
| 2006/0151687 A1 * | 7/2006 | Miller et al. .................. 250/282 |
| 2006/0255258 A1 * | 11/2006 | Wang et al. ................... 250/282 |
| 2007/0208545 A1 * | 9/2007 | Wittkowski .................... 702/189 |
| 2007/0278395 A1 * | 12/2007 | Gorenstein et al. ........... 250/282 |
| 2007/0282537 A1 | 12/2007 | Freitas et al. |
| 2008/0070314 A1 | 3/2008 | Geromanos et al. |
| 2008/0135744 A1 * | 6/2008 | Geromanos et al. .......... 250/281 |
| 2008/0142696 A1 * | 6/2008 | Geromanos et al. .......... 250/282 |
| 2009/0065686 A1 * | 3/2009 | Shilov et al. ................ 250/252.1 |
| 2009/0179147 A1 * | 7/2009 | Milgram et al. .............. 250/282 |
| 2009/0283673 A1 * | 11/2009 | Shilov et al. .................. 250/282 |
| 2009/0294645 A1 * | 12/2009 | Gorenstein et al. ........... 250/282 |
| 2010/0187414 A1 * | 7/2010 | Gorenstein et al. ........... 250/282 |
| 2013/0105682 A1 * | 5/2013 | Geromanos et al. .......... 250/282 |

OTHER PUBLICATIONS

PCT International Written Opinion Report for Application No. PCT/US09/45373, dated Jul. 31, 2009.

* cited by examiner

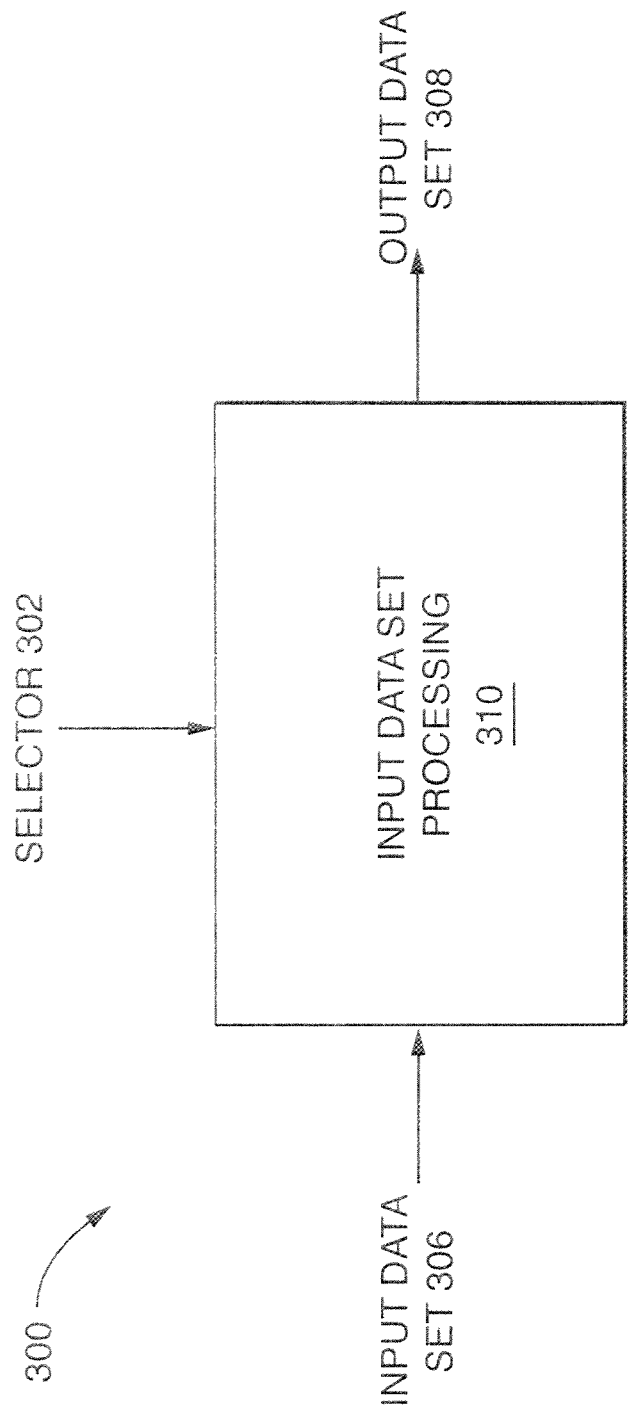

TECHNIQUES FOR PERFORMING RETENTION-TIME MATCHING OF PRECURSOR AND PRODUCT IONS AND FOR CONSTRUCTING PRECURSOR AND PRODUCT ION SPECTRA

CROSS-REFERENCE TO RELATED APPLICATIONS

This application is the National Stage of International Application No. PCT/US2009/045373, filed May 28, 2009, which claims priority to U.S. Provisional Application No. 61/056,871, filed May 29, 2008, all of which are hereby incorporated by reference.

TECHNICAL FIELD

The invention generally relates to analyses of compounds, and, more particularly, to instruments and methods for polypeptide analyses.

BACKGROUND INFORMATION

Proteomics generally refers to studies involving complex mixtures of proteins derived from biological systems. Proteomic studies often focus on identification of proteins or determination of changes in the state of a biological system. Identification and quantification of proteins in complex biological samples is a fundamental problem in proteomics.

Liquid chromatography coupled with mass spectrometry (LC/MS) has become a fundamental tool in proteomic studies. Separation of intact proteins or of their proteolyzed peptide products by liquid chromatography (LC) and subsequent analysis by mass spectrometry (MS) forms the basis of many common proteomic methodologies. Methods that measure changes in the expression level of proteins are of great interest as they can form the basis of biomarker discovery and clinical diagnostics.

Rather than directly analyzing intact proteins, proteins of are typically digested to produce a specific set of proteolytic peptides. The resulting peptides are then often characterized via LC/MS analysis. A common enzyme used for digestion is trypsin. In tryptic digestion, the proteins present in a complex mixture are cleaved to produce peptides as determined by the cleavage specificity of the proteolytic enzyme. From the identity and concentration of the observed peptides, available algorithms serve to identify and quantify the proteins in the sample.

In LC/MS analysis, the peptide digest is first separated and analyzed by LC separation followed by MS analysis. Ideally, the mass of a single peptide, measured with sufficient accuracy, provides a unique identification of the peptide. In practice, however, achieved mass accuracies typically are on the order of 10 ppm or larger. In general, such mass accuracy is not sufficient to uniquely identify a peptide using the mass measurement alone.

For example, in the case of a mass accuracy of 10 ppm, on the order of 10 peptide sequences are identified in a search of a typical database of peptides sequences. This number of sequences would increase significantly if search restraints on mass accuracy were lowered, or searches for chemical or post-translational modifications, losses of $H_2O$ or $NH_3$, and point mutations were allowed, for example. Thus, if a peptide's sequence is modified by either a deletion or substitution, use of only the precursor's mass for identification of the peptide will lead to a false identification. A further complication arises from the possibility that two peptides can have the same amino acid composition but have different sequences.

In the case of peptide precursors, product fragments can be obtained by fragmentation at a single peptide bond in the precursor. Such a single fragmentation produces two subsequences. The fragment containing the peptide's C-terminal, if ionized, is termed a Y-ion, and the fragment containing the peptide's N-terminal, if ionized is termed a B-ion.

Proteins are often identified by comparing analysis data to a database that associates protein identities with information about fragments of the proteins, such as masses of the fragments. For example, if a theoretical peptide mass from a database lies within a mass search window of the mass of a precursor measured in the data, it is deemed a hit.

The search can provide a list of possible matching peptides found in the database. These possible matching database peptides may or may not be weighted by statistical factors. The possible outcomes of such a search are that no possible matching database peptides are identified, one possible matching database peptide is identified, or more than one possible matching database peptide are identified. The higher the resolution of the MS, assuming proper instrument calibration, the smaller the ppm threshold, and consequently, the fewer the false identifications. If there are one or more matches to the peptides in the database, peptide-fragment ion data may be used to validate a match.

During a search, multiple charge states and multiple isotopes can be searched. Further, empirically produced confidence rules can be applied to help identify valid matches.

SUMMARY OF THE INVENTION

In accordance with one aspect of the inventions are a method and computer readable medium for matching a precursor ion with one or more related product ions. A plurality of input data sets is obtained from a plurality of injections. Each of the plurality of input data sets include a same precursor ion and one or more product ions. The plurality of input data sets is normalized in accordance with a single retention time for the precursor ion. For each of the plurality of input data sets, it is determined which product ions are within a predetermined retention time window with respect to the single retention time for said precursor ion. If a product ion is within the predetermined retention time window in at least one of the plurality of input data sets, it is determined that the product ion is related to the precursor ion having the single retention time.

In accordance with another aspect of the invention is a method for matching precursors with related product ions. The method includes performing a plurality of injections; tracking each of said precursors across the plurality of injections to determine which of said plurality of injections include each of said precursors in accordance with criteria including a retention time and a mass associated with said each precursor; determining, for each of said precursors, a set of related product ions, each of said related product ions having a retention time within a predetermined retention time window with respect to said retention time of said each precursor in at least one of said plurality of injections; and determining, for each of said related product ions of each of said precursors, an intensity sum, wherein said intensity sum is determined by adding one or more intensities of said each related product ion, each of said one or more intensities corresponding to an intensity of said each related product ion in a different one of said plurality of injections including said each precursor.

In accordance with another aspect of the invention is an apparatus for analyzing a sample including a chromatography module; a mass-spectrometry module in communication with said chromatography module; and a control unit in communication with said chromatography module and said mass spectrometry module. The control unit includes at least one processor and a memory for storing a plurality of instructions executed by said processor. The plurality of instructions cause the processor to perform: tracking each of said precursors across a plurality of injections to determine which of said plurality of injections include each of said precursors in accordance with criteria including a retention time and a mass associated with said each precursor; determining, for each of said precursors, a set of related product ions, each of said related product ions having a retention time within a predetermined retention time window with respect to said retention time of said each precursor in at least one of said plurality of injections; and determining, for each of said related product ions of each of said precursors, an intensity sum, wherein said intensity sum is determined by adding one or more intensities of said each related product ion, each of said one or more intensities corresponding to an intensity of said each related product ion in a different one of said plurality of injections including said each precursor.

In accordance with yet another aspect of the invention is a method of matching a precursor ion with one or more related product ions. The method includes providing a plurality of input data sets obtained from a plurality of injections, each of said plurality of input data sets including a same precursor ion and one or more product ions; normalizing said plurality of input data sets in accordance with a single retention time for said precursor ion; for each of said plurality of input data sets, determining which product ions have corresponding retention times that are within a predetermined retention time window with respect to said single retention time for said precursor ion; and performing a set union operation with respect to product ions included in said plurality of input data sets so that if a product ion is determined by said determining step to have a corresponding retention time within the predetermined retention time window with respect to said single retention time in at least one of said plurality of input data sets, said product ion is included in a resulting set of product ions determined as being related to said precursor ion having said single retention time.

In accordance with another aspect of the invention is a method and computer readable medium for matching a precursor ion with one or more related product ions. A plurality of input data sets obtained from a plurality of injections is provided. Each of the plurality of input data sets include a same precursor ion having a first retention time and one or more product ions having a retention time within a predetermined retention time window with respect to said first retention time for said precursor ion. A first of the input data sets is selected in which an intensity of said precursor ion is a maximum with respect to an intensity of said precursor in others of said plurality of input data sets. A first set of product ions is determined wherein each product ion in the first set is in said first input data set selected by said selecting and has a retention time within said predetermined retention time window with respect to said first retention time. For each product ion in said first set, a first result is determined as which of said plurality of input data sets include said each product ion having a retention time that is within said predetermined retention time window with respect to said first retention time, and an intensity sum is determined for said each product ion as a sum of intensities for said product ion across input data sets in said first result. The first set of product ions are related to said precursor and each of said product ions in said first set has an intensity sum as determined by said step of determining an intensity sum.

In accordance with another aspect of the invention are a method and computer readable medium for matching a precursor ion with one or more related product ions. A plurality of input data sets obtained from a plurality of injections is provided. Each of the plurality of input data sets includes a same precursor ion having a first retention time and one or more product ions having a retention time within a predetermined retention time window with respect to said first retention time for said precursor ion. A first set of product ions having a retention time within said predetermined retention time window with respect to said first retention time in at least one of said plurality of input data sets is determined. Each product ion in said first set has an intensity that is a sum of intensities of said product ion across input data sets in said plurality that include said each product ion, and wherein said each product ion has a retention time within said predetermined retention time window with respect to said first retention time. A first of the input data sets is selected in which an intensity of said precursor ion is a maximum with respect to an intensity of said precursor in others of said plurality of input data sets. A second set of product ions is determined wherein each product ion in said second set is included in said first input data set selected by said selecting and has a retention time within said predetermined retention time window with respect to said first retention time. Removed from the first set are product ions are which are not included in said second set. After removing the product ions from the first set, the first set includes product ions related to said precursor.

In accordance with another aspect of the invention is a method for determining product ions related to a precursor ion. The method includes providing a plurality of input data sets obtained from a plurality of injections, each of said plurality of input data sets including a same precursor ion having a first retention time and one or more product ions having a retention time within a predetermined retention time window with respect to said first retention time for said precursor ion; providing a plurality of retention time matching and product ion selection techniques, each of said plurality of retention time matching and product ion selection techniques performing processing to combine information from said plurality of input data sets regarding related product ions determined to be related to said precursor, said related product ions each having a retention time within said predetermined retention time window with respect to said first retention time, said plurality of retention time matching and product ion selection techniques including a first technique which determines that a product ion is related to said precursor ion if said product ion has a retention time within the predetermined retention time window with respect to said first retention time in at least one of the plurality of input data sets; selecting at least one of the plurality of retention time matching and product ion selection techniques; and processing said plurality of input data sets using said at least one selected retention time matching and product ion selection technique to determine product ions related to said precursor ion.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 3 is a block diagram illustrating processing that may be performed on an input data set in an embodiment of the invention;

DESCRIPTION

Figure 1:
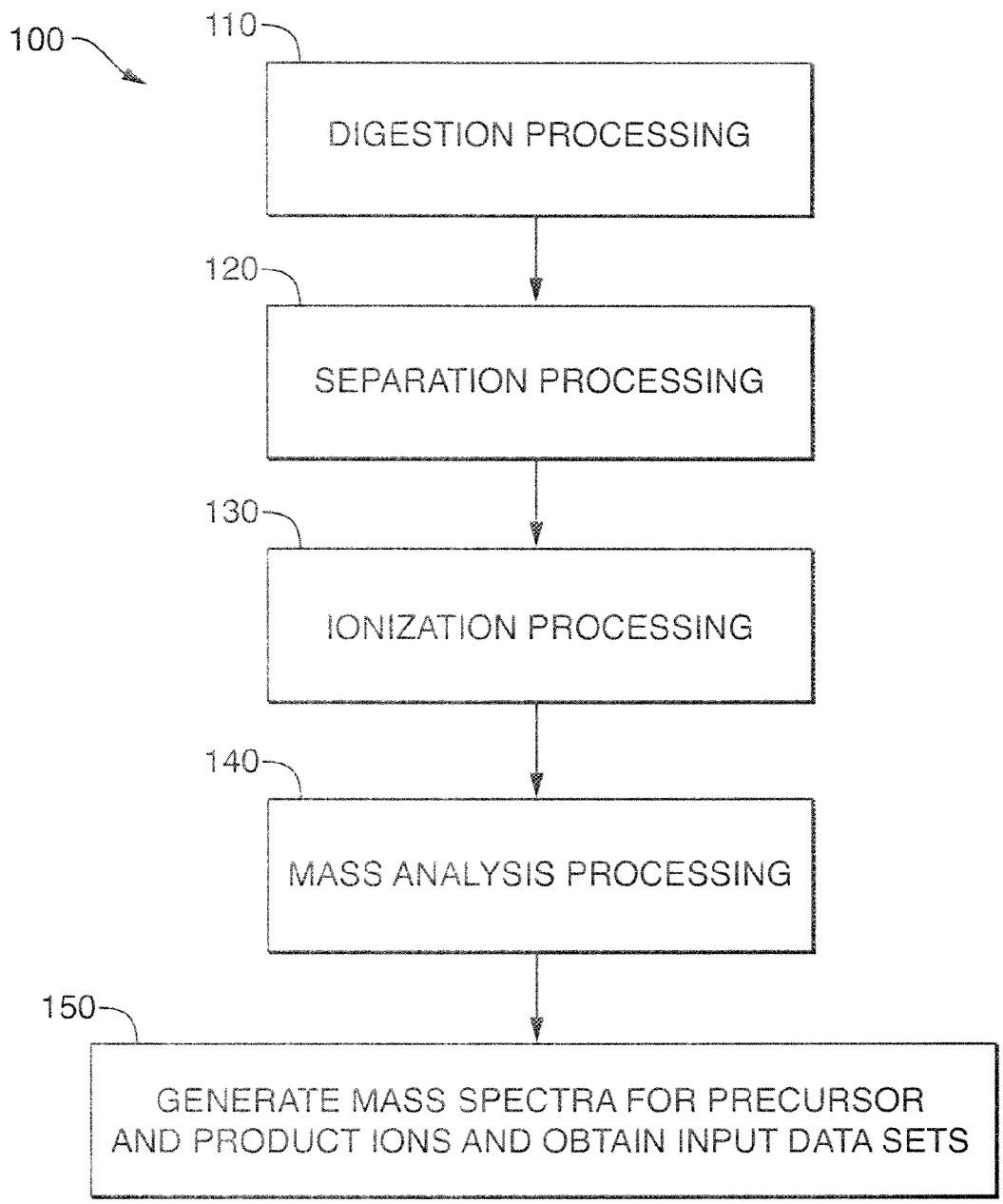
FIG. 1 is a flow diagram of a method for performing chemical analyses of compounds, in accordance with one embodiment of the invention.

As used herein, the following terms generally refer to the indicated meanings:

Protein—a specific primary sequence of amino acids assembled as a single polypeptide.

Peptide—a specific sequence of amino acids assembled as a single polypeptide contained within the primary sequence of a protein.

Tryptic peptides—peptides generated from a protein sequence that result from enzymatic cleavage of the protein by trypsin. In the ensuing description, digest peptides are referred to as tryptic peptides for convenience. It should be understood, however, that embodiments of the present invention apply to other peptide digestion techniques. Moreover, the term "digestion" is used herein to refer generally to any suitable method for degrading or cleaving a polypeptide, including, for example, the use of cellular enzymes (proteases) and intramolecular digestion. The term "proteolytic," as used herein, refers to any enzyme which digests or lyses large proteins into smaller sections or amino acids.

Precursor peptides—tryptic peptides (or other protein cleavage products) that are generated using a protein-cleavage protocol. The precursors are optionally separated chromatographically and passed to a mass spectrometer. An ion source ionizes these precursor peptides to typically produce a positively charged, protenated form of the precursor. The mass of such positively charged protenated precursor ion is herein referred as the "mwHPlus" or "MH+" of the precursor. In the following, the term "precursor mass" refers generally to the protenated, mwHPlus or MH+ mass of the ionized, peptide precursor.

Fragments or product ions—Multiple types of fragments or product ions can occur in LC/MS analyses. In the case of tryptic peptide precursors, fragments can include polypetide ions that are produced from collisional fragmentation of the intact peptide precursors and whose primary amino acid sequence is contained within the originating precursor peptide. Y-ions and B-ions are examples of such peptide fragments. Fragments of tryptic peptides can also include immonium ions, functional groups such as a phosphate ion ($PO_3$), mass tags cleaved from a specific molecule or class of molecules, or "neutral loss" of water ($H_2O$) or ammonia ($NH_3$) molecules from the precursor.

Y-ions and B-ions— If a peptide fragments at the peptide bond, and if a charge is retained on the N terminal fragment, that fragment ion is termed a B-ion. If the charge is retained on the C terminal fragment, the fragment ion is termed a Y-ion. A more comprehensive list of possible fragments and their nomenclature is provided in Roepstorff and Fohlman, Biomed Mass Spectrom, 1984; 11(11):601 and Johnson et al, Anal. Chem. 1987, 59(21): 2621:2625.

Retention time—in context, typically refers to the point in a chromatographic profile at which an entity reaches its maximum intensity.

Ions—each peptide typically appears in an LC/MS analysis as an ensemble of ions due to the natural abundance of the isotopes of the constituent elements. An ion has a retention time and an m/z value. The mass spectrometer (MS) detects only ions. The LC/MS technique produces a variety of observed measurements for every detected ion.

This includes: the mass-to-charge ratio (m/z), mass (m), the retention time, and the signal intensity of the ion, such as a number of ions counted.

MwHPlus—The neutral, monoisotopic mass of the peptide plus the weight of one proton, 1.007825 amu.

Generally, an LC/MS analysis optionally provides an empirical description of a peptide in terms of its mass, charge, retention time and total intensity. When a peptide elutes from the chromatographic column, it elutes over a specific retention time period and reaches its maximum signal at a single retention time. After ionization and (possible) fragmentation, the peptide appears as a related set of ions. The different ions in the set correspond to different isotopic compositions and charges of the common peptide. Each ion within the related set of ions produces a single peak retention time and peak shape. Since these ions originate from a common peptide, the peak retention time and peak shape of each ion is identical, within some measurement tolerance. The MS acquisition of each peptide produces multiple ion detections for all isotopes and charge states, all sharing the same peak retention-time and peak shape within some measurement tolerance.

In an LC/MS separation, a single peptide (precursor or fragment) produces many ion detections, which appears as a cluster of ions, at multiple charge states. Deconvolution of these ion detections from such a cluster, indicates the presence of a single entity of a unique monoisotopic mass, at a specific retention time, of a measured signal intensity, in a charge state.

Protein Database—In some embodiments of the present invention, an analyst utilizes a database of proteins. In a typical database, each included protein is described by its primary sequence of amino acids. An analyst might choose a database that is intended to closely match proteins under study. For example, an *E. Coli* database could be compared to data obtained from a cell lycate of *E. Coli*. Similarly, a human serum database could be compared to data obtained from human serum. A user could choose a subset database. A user could choose a superset database, such as all proteins listed in the SwissProt database produced by the Swiss-Prot groups at the Swiss Institute of Bioinformatics (SIB) and the European Bioinformatics Institute (EBI). A user could choose a data a base that contains simulated proteins, described by random sequences of amino acids. Such random databases are used in control studies to evaluate or calibrate protein identification systems and search algorithms. A user could choose a database that combines both naturally occurring and artificial sequences. From the protein database, one can infer from each sequence, the sequence and masses of tryptic precursor ions, Y- and B-ions, and other possible fragment ions that would result from those precursors.

FIG. 1 is a flow diagram of a method 100 for performing chemical analyses of compounds as may be performed in an embodiment in connection with the techniques herein. The method 100 includes digesting 110 one or more compounds of a reference sample into component fragments of the compounds, separating 120 the components, ionizing 130 and mass analyzing 140 at least some of the separated components, and generating 150 mass spectra for the precursor and product or fragment ions of at least one compound in the sample to obtain one or more input data sets for use with the techniques herein. The input data set may be processed in accordance with the techniques herein to perform retention time matching of precursors and related product ions. The techniques herein perform retention time matching and product ion selection to determine a set of product ions which are related to a precursor. As described in more detail in following paragraphs, the steps of 100 may be performed one or more times for each of one or more samples.

Preferably, when repeating the steps of 100 on the subject sample, effectively the same pre-selected method(s) for digestion, chromatographic separation, and/or ionization are used for digesting 110, separating 120, ionizing 130, and mass analyzing 140 of the subject sample as used for the reference sample.

Some preferred uses of the method 100 are directed toward protein-related analyses. Thus, for convenience, the following description refers to proteins and related fragments, and utilizes examples of analyses of compounds that are polypeptides, such as proteins; in these examples, a protein is digested into component fragments that are precursor fragments of the protein. Precursors, in turn, are ionized to form precursor ions and optionally are themselves fragmented into product ions in preparation for mass analysis.

Although the description focuses on examples related to polypeptides, such examples are not intended to limit the scope of the invention to analyses of polypeptides; one having ordinary skill in the chemical-analysis arts will recognize that principles of the invention are applicable to analyses of other chemical compounds.

Digesting 110 is accomplished via any suitable technique for cleaving proteins, including known techniques. For example, as described above, a protein is digested into precursor polypeptides or amino acids through use of one or more enzymes such as trypsin. Fragments of a protein or polypeptide are herein generally referred to as "precursors." Such a fragment is a precursor in the sense that it is optionally used in additional analyses subsequent to chromatographic separation. As described in more detail below, precursor fragments are optionally ionized and/or further fragmented into product fragments.

Separating 120 is accomplished by any suitable chromatographic-related technique, including known techniques such as reverse-phase chromatography, gel-permeation chromatography, size-exclusion chromatography, and electrophoresis. Separating 120 provides values associated with retention times of the proteins and/or precursors obtained from digesting 110 proteins in a sample.

In preparation for mass analyzing 140 the eluent of a chromatographic separation 120, the eluent from the separating 120 process is subjected to an ionizing 130 process. Any suitable ionizing 130 process is optionally used, including known techniques such as electrospray ionization and MALDI. During the ionizing 130 process, at least some of the precursors are ionized to form precursor ions. For example, a single protein molecule is digested 110 to form twenty precursor fragments, of which ten are ionized during ionizing 130. As described in more detail below, precursors may be further fragmented to obtain product ions.

Mass analyzing 140 provides values associated with mass and values associated with ion intensity of the precursor ions. Mass analyzing 140 is performed via any suitable mass-analysis techniques, including known techniques. Such techniques include magnetic-sector spectrometry and time-of-flight spectrometry.

As illustrated in step 150, information obtained from the above-described analysis step 140 may be in the form of mass spectra for the precursor and product ions used to obtain an input data set which may be further processed using the techniques described herein.

In some embodiments performing the steps of FIG. 1, the data included in the input data of step 150 may be obtained using an LC/MS system. For example, as described in more detail with reference to FIGS. 2A and 2B, an eluent output by the liquid chromatograph is introduced into a mass spectrometer through an electrospray interface. Optionally, a first quadrupole of a triple-quadrupole MS instrument functions as an ion guide. An alternating voltage is applied to a collision cell of the instrument. Spectra are collected of precursors ions and of their fragment (product) ions, for example in an alternating fashion, as described below.

Preferably, both precursor ions and associated product ions are formed from the same precursor material obtained from the separating 120 process. In this manner, both precursor ions and associated product ions will have the same retention time data determined from the separating 120 process. Product ions may thus be relatively readily associated with the precursor from which they arose. If two or more injections of a sample are performed, precursor-ion and product-ion data may be obtained from different injections.

Any suitable method, including known methods, may be used to obtain both precursor and product ions from a single sample injection. Such methods provide effectively simultaneous mass analysis of both precursor and product ions. For example, a portion of an eluted precursor is fragmented to form product ions, and the precursor and product ions are substantially simultaneously analyzed, either at the same time or, for example, in rapid succession.

As an alternative example, two or more alternating portions of the peak are used respectively for precursor and product analysis. A portion of a peak's precursor material is ionized and analyzed, and then a next portion is dissociated into product fragments that are analyzed. In one embodiment, alternating portions of an eluting precursor are sampled to alternately obtain data for the precursor ion and its product ions. The obtained data permits reconstruction of a peak shape to permit measurement of an accurate retention time value for both the eluted precursor and its associated product.

Moreover, for example, peak shape, width, and/or time of reconstructed peaks associated with precursor ions and with product ions are optionally compared to determine which product ions are associated with a particular product ion.

One approach to such alternating, effectively simultaneous analysis, is described in U.S. Pat. No. 6,717,130 to Bateman, et al. ("Bateman"), which is incorporated herein by reference and describes application of an alternating voltage to a collision cell to regulate fragmentation. Additional description of related features is provided below with reference to FIGS. 2A and 2B.

Thus, the technique described in the Bateman or other suitable technique uses retention-time observations to support the determination of which product ions are derived from a particular precursor. The product ions are associated with their precursor ion in response to matching retention-time values.

For example, a threshold retention-time difference is selected; if the difference in retention times of a product ion and a precursor ion is less than the threshold value, the product is determined to be derived from the precursor. For example, one suitable threshold value is equal to one tenth the retention-time peak width of the precursor ion. The retention-time value of an ion is optionally defined as the time value of the peak maximum of the peak that was observed for that ion.

Figure 2A:
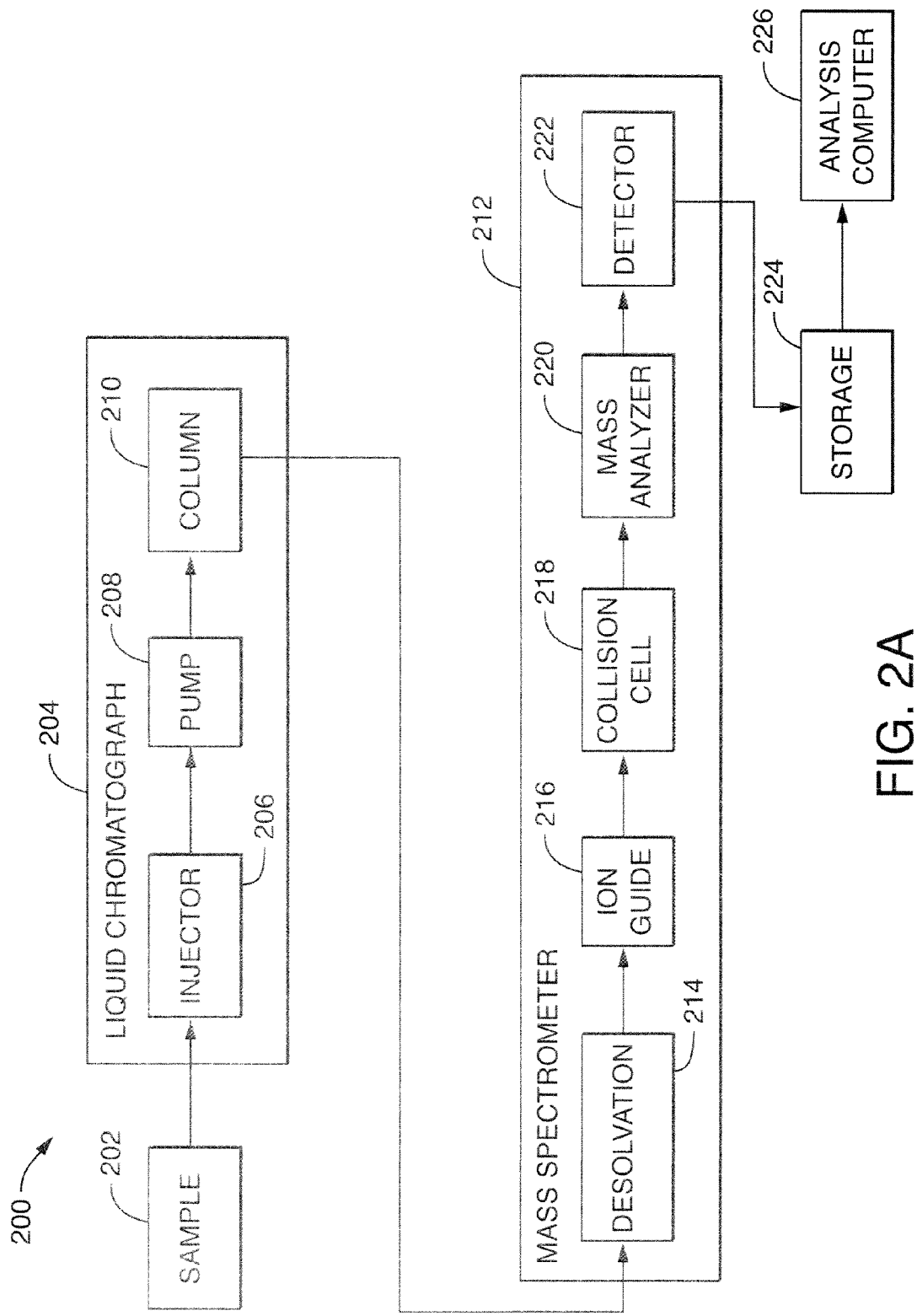
FIG. 2A is a block diagram of an LC/MS system, in accordance with one embodiment of the invention.
Figure 2B:
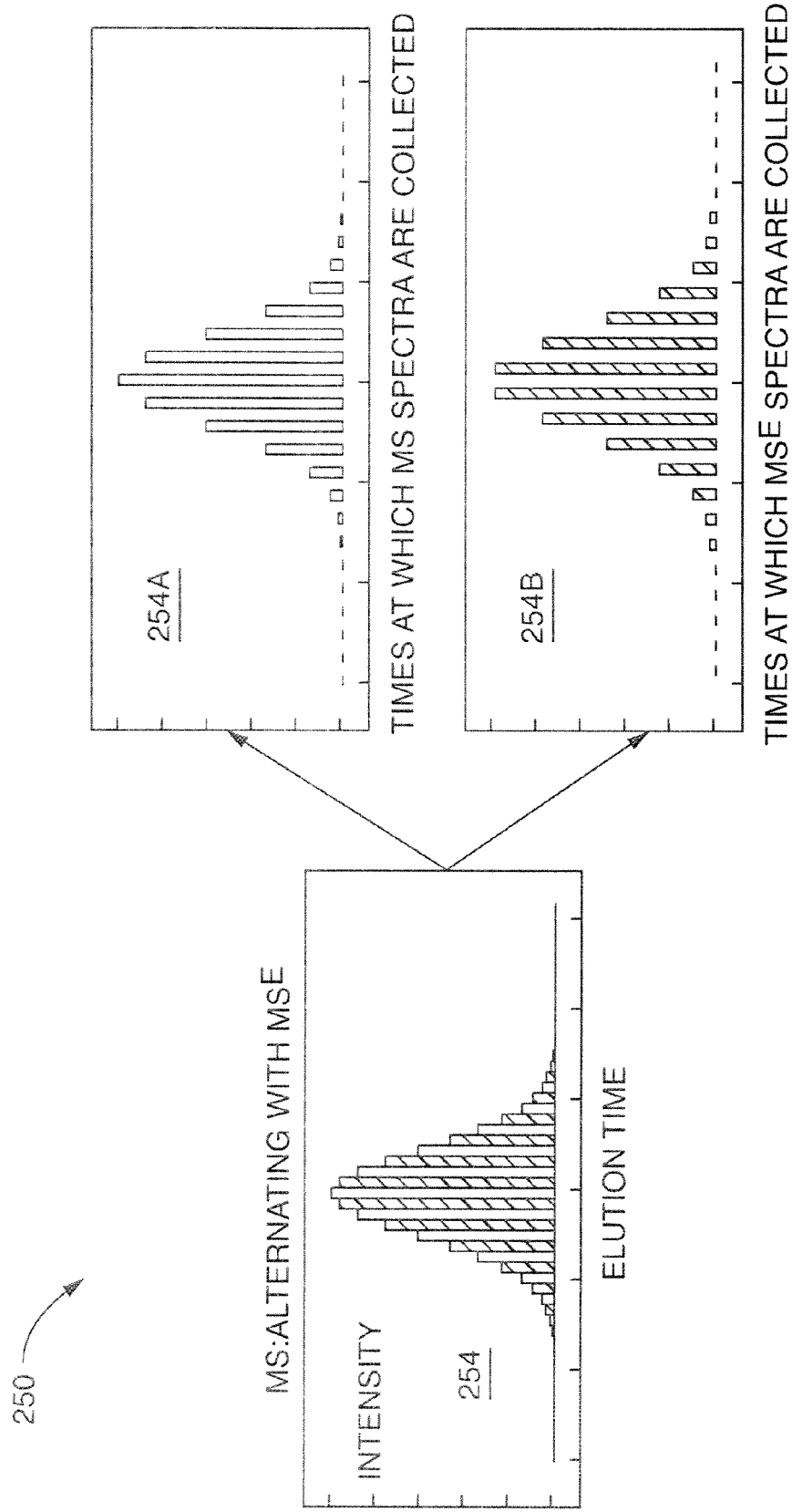
FIG. 2B shows three related graphs, which illustrate the collection of mass spectra in accordance with one embodiment of the invention.

Referring next to FIGS. 2A and 2B, some embodiments of the invention relate to LC/MS instruments. FIG. 2A is a block diagram of an LC/MS system 200, according to one embodiment of the present invention. The instrument includes a chromatography module 204 and a mass-spectrometer module 212 that receives an eluent from the chromatography module 204. The LC module 204 includes an injector 206 that receives a sample 202, a pump 208 and a column 210, the MS module 212 includes a desolvation/ionization device 214, an ion guide 216, a mass analyzer 220, and a detector 222. The system 200 also includes a data storage unit 224 and a computer module 226.

In operation, the sample 202 is injected into the LC module 204 via the injector 206. The pump 208 pumps the sample through the column 210 to separate the mixture into component parts according to retention time through the column 210.

The output from the column 210 is input to a mass spectrometer 212 for analysis. Initially, the sample is desolvated and ionized by the desolvation/ionization device 214. Any desolvation technique can be employed, including, for example, a heater, a gas, and a heater in combination with a gas or other desolvation technique. Ionization can be by any suitable ionization technique, including for example, electrospray ionization (ESI), atmospheric pressure chemical ionization (APCI), or other ionization technique. Ions resulting from the ionization are fed to a collision cell 218 by the ion guide 216.

The collision cell 218 is used to fragment the ions. In preferred embodiments, the collision cell 218 is operated in a switching mode to support observation of both precursor ions and product ions of the same eluting precursor material.

Any suitable switching techniques may be used, including known techniques. Some embodiments of the invention preferably use a fragmentation protocol in which a relatively simple alternating voltage cycle is applied to the cell 218. This switching is done at a high enough frequency so that multiple high- and multiple low-energy spectra are contained within a single chromatographic peak. Unlike some other switching protocols, the cycle is independent of the content of the data.

For example, as described in the '130 patent, an alternating voltage is applied to the collision cell 218 to cause fragmentation. Spectra are collected for the precursors (no collisions) and fragments (results of collisions.)

Alternative embodiments utilize other means for fragmentation, such as any suitable collision fragmentation or reaction device, including any suitable known device. Some optional devices include: (i) a Surface Induced Dissociation ("SID") fragmentation device; (ii) an Electron Transfer Dissociation fragmentation device; (iii) an Electron Capture Dissociation fragmentation device; (iv) an Electron Collision or Impact Dissociation fragmentation device; (v) a Photo Induced Dissociation ("PID") fragmentation device; (vi) a Laser Induced Dissociation fragmentation device; (vii) an infrared radiation induced dissociation device; (viii) an ultraviolet radiation induced dissociation device; (ix) a nozzle-skimmer interface fragmentation device; (x) an in-source fragmentation device; (xi) an ion-source Collision Induced Dissociation fragmentation device; (xii) a thermal or temperature source fragmentation device; (xiii) an electric field induced fragmentation device; (xiv) a magnetic field induced fragmentation device; (xv) an enzyme digestion or enzyme degradation fragmentation device; (xvi) an ion-ion reaction fragmentation device; (xvii) an ion-molecule reaction fragmentation device; (xviii) an ion-atom reaction fragmentation device; (xix) an ion-metastable ion reaction fragmentation device; (xx) an ion-metastable molecule reaction fragmentation device; (xxi) an ion-metastable atom reaction fragmentation device; (xxii) an ion-ion reaction device for reacting ions to form adduct or product ions; (xxiii) an ion-molecule reaction device for reacting ions to form adduct or product ions; (xxiv) an ion-atom reaction device for reacting ions to form adduct or product ions; (xxv) an ion-metastable ion reaction device for reacting ions to form adduct or product ions; (xxvi) an ion-metastable molecule reaction device for reacting ions to form adduct or product ions; and (xxvii) an ion-metastable atom reaction device for reacting ions to form adduct or product ions.

The output of the collision cell 218 is input to a mass analyzer 220. The mass analyzer 220 is any suitable mass analyzer, including quadrupole, time-of-flight (TOF), ion trap, magnetic sector mass analyzers as well as combinations thereof. The detector 222 detects ions emanating from the mass analyzer 220. The detector 222 is optionally integral with mass analyzer 220. For example, in the case of a TOF mass analyzer, the detector 222 is optionally a microchannel plate detector that counts intensity of ions, i.e., counts numbers of impinging ions. The storage medium 224 provides permanent storage for storing the ion counts for analysis. For example, storage medium 224 is an internal or external computer disk. The analysis computer 226 analyzes the stored data. Data can also be analyzed in real time without requiring storage in a storage medium 224. In that case, the detector 222 passes data to be analyzed directly to computer 226 without first storing it to permanent storage.

The collision cell 218 performs fragmentation of the precursor ions. Fragmentation can be used to determine the sequence of a peptide and subsequently lead to the identity of the originating protein.

The collision cell 218 utilizes a gas, such as nitrogen. When a charged peptide interacts with the gas' atoms, the resulting collisions can fragment the peptide by breaking it up at one or more characteristic bonds. The most common resulting fragments are described as Y- or B-ions. Such fragmentation can be accomplished as on-line fragmentation by switching the voltage in a collision cell between a low voltage state (low energy) which obtains MS spectra of the peptide precursor, with a high voltage state (high energy) which obtains MS spectra of the collisionally induced fragments of the precursors. High and low voltage are referred to as high and low energy, since a voltage is used to impart kinetic energy to an ion.

The chromatographic module 204 includes any suitable chromatography instrument(s), including known instruments, such as column-based instruments. Suitable columns include columns known to one having ordinary skill in the chromatographic arts. The column can be formed from, for example, metallic or insulating materials. Suitable materials include known materials such as steel, fused silica, or lined materials. The column can include more than one column, disposed in serial and/or parallel configurations. For example, the column can be a capillary column and can include multiple capillary tubes.

The computer module 226 is in data communication with other components of the system 200 via wired and/or wireless means, such as those known in the data-communication arts. The module 226 receives process data, for example, from the mass-spectrometer module 212, and provides control signals. The module 226 is optionally configured to implement methods described herein, such as the method 100 for chemical analysis described above, and/or the different techniques described herein for further processing the input data set acquired as a result of the step 150 of FIG. 1. The module 226, in various illustrative embodiments, is implemented in software, firmware, and/or hardware (e.g., as an application-specific integrated circuit), and includes, if desired, a user interface. The module 226 includes and/or is in communication with storage component(s), such as the storage unit 224.

Suitable implantations of the module 226 include, for example, one or more integrated circuits, such as microprocessors. A single integrated circuit or microprocessor in some alternative embodiments includes the module 226 and other electronic portions of the system 200. In some embodiments, one or more microprocessors implement software that enables the functions of the module 226. In some embodiments, the software is designed to run on general-purpose equipment and/or specialized processors dedicated to the functionality herein described.

An LC/MS experiment can produce as one of its outputs a mass chromatogram. A mass chromatogram is a set or group of responses (intensities) recorded as a function of time at a specific mass value. In a mass chromatogram, the mass value may be the central value within a range. That is, the intensity at a given time may be obtained by combining intensities collected over a specified range of mass values. Typically, a mass chromatogram contains one or more chromatographic peaks.

A single molecule, or chemical entity, has a specific mass. In an LC/MS experiment the ionized form of that molecule is observed as a chromatographic peak at the mass value of that ion divided by its charge (mass-to-charge ratio). A chromatographic peak has a peak profile, or elution profile. The chromatographic peak profile can be characterized using several features, including an apex retention time, a peak width, a lift off time and a touch down time. A chromatographic peak width can be described as a width at a specific peak height (FWHM, width at 50% height), or a width between inflection points, or as a standard deviation. The apex intensity or chromatographic peak height is the maximum intensity found in a chromatographic peak profile. Generally, the apex intensity is baseline corrected.

A molecule in an eluent that is separated by a chromatographic separation, and elutes from the column is referred to as the common eluting molecule or originating molecule. The originating molecule is ionized through the ionization source of the mass spectrometer. The resulting ions are measured in an LC/MS or LC/MS$^E$ spectra. It should be noted that depending on the context, LC/MS may generally refer to the LC/MS process of data acquisition. In connection with data collected and represented such as in the form of spectra, for example, as in connection with FIG. 2B described herein, MS spectra may refer to spectra from unfragmented precursors. MS$^E$ spectra may refer to high-energy spectra (i.e., spectra from fragmented precursors, that is, product ions, labeled "MS$^E$". As a result of isotopic composition and or fragmentation processes, each originating molecule can give rise to multiple categories of ions, each having a unique value of mass and charge. The ion corresponding to the originating molecule is termed the precursor ion, or just the precursor.

In peptide digests the originating molecule is a peptide and the ion corresponding to the peptide is referred to as the precursor. Any ion derived from the originating molecule, whether the procursor or a fragment, must have the same retention time and chromatographic peak profile as the precursor.

In an LC/MS experiment an ion can be described and/or referred to by its retention time, mass-to-charge ratio, and intensity. A single molecule can appear in an LC/MS chromatogram as a cluster of ions. A peptide gives rise to one or more ion clusters. Each cluster corresponds to a different charge state (e.g., Z=1 or Z=2). Each ion in a cluster corresponds to a different isotopic composition of the peptide. In a cluster of ions from a common peptide, the monoisotope is the ion having the lowest mass, where all the isotopes are in their most abundant, low mass state. Since the ions in the cluster come from a common originating molecule, they must share a common retention time and peak profile.

An originating molecule can give rise to multiple ions due to isotope and charge effects. Additional, important sources of ions are fragments of the originating molecule. These fragments arise from processes that break up the originating molecule. These processes can occur in the ionization source or in a collision cell. Because fragment ions derive from a common eluting, originating molecule, they must have the same chromatographic retention time and peak profile as the originating molecule.

Generally, if an originating molecule gives rise to N ions, and if these are adequately resolved by the mass spectrometer, then there can be N mass chromatograms, where each mass chromatogram contains a peak, a chromatographic profile of an ion that derives from the originating molecule. The retention time and peak profile of each of these N ions will be identical. The term common-retention-time-entity refers to all ions of an originating molecule that, in an LC/MS separation, give rise to chromatographic peaks all having the same retention times and peak shapes.

The retention time and peak shapes of ions that derive from a common originating molecule are the same because the time of ion formation, fragmentation, and ion detection is generally much shorter then the peak width of the originating molecule. For example, a typical chromatographic peak width, measured at full-width at half-maximum (FWHM) is 5 to 30 seconds. The time of ion formation, fragmentation, and detection is typically sub milliseconds. Thus on a chromatographic time scale, the time of ion formation is an instantaneous process. It follows that differences in observed retention times of the ions that derived from an originating molecule is effectively zero. That is, sub-millisecond retention time differences between ions that derived from an originating molecule are small compared to the chromatographic peak width.

The ions that are associated with an originating molecule fall into one of several categories. An ion derived from an originating molecule can be a precursor, a fragment of the precursor, or a fragment of a fragment, or a neutral loss of any of the above masses. Any of these masses can be seen in one or more discrete isotopic states, and in one or more charge states.

In the case of peptides, a given peptide is generally seen to be a cluster of ions, each in a distinct isotopic state, and each in one or more charge states. Ideally the ionization source produces precursors that are a protenated form of the neutral originating molecule. One or more protons can be attached to the neutral molecule and thus the precursors can be one or more mass units higher than the neutral with charge $Z=+1$, or $+2$, etc. In practice, this precursor (termed mwHPlus) may be accompanied by lower mass entities that result from the loss of neutral molecules such as water, ammonia, or phosphate. Fragmentation can occur in the source, yielding, typically, Y- or B-ions. Fragmentation can be also be deliberately induced by down-stream interactions with gas molecules in a collision cell.

With respect to ions that are generated from collision-induced disassociation of intact precursor ions, the fragment product ions are associated with their parent precursor ion. By using the mass spectrometer in a High-Low Data Acquisition Mode, this association is accomplished without requiring the instrument to pre-select a single precursor for subsequent fragmentation. More specifically, associated ions are appropriately grouped when multiple precursors are fragmenting simultaneously, at essentially the same retention time. Thus, embodiments of the present invention can assign product ions to their respective precursor when there is more than one precursor fragmenting at the same moment in time.

The method of the current invention can be applied to mixtures other than that of peptides, provided originating molecules give rise to precursor ions and fragment ions. Thus embodiments of the present invention can be used in proteomics, metabolomics, and metabonomics.

The retention time and chromatographic peak profile of a molecule (peptide, metabolite, natural product) eluting from a chromatographic support matrix, such as column 210, is a function of the physical interaction of that molecule between the support matrix and mobile phase. The degree of interaction that a molecule has between the support matrix and the mobile phase dictates the chromatographic profile and retention time for that molecule. In a complex mixture, each molecule is chemically different. As a result, each molecule can have a different affinity for the chromatographic matrix and the mobile phase. Consequently, each can exhibit a unique chromatographic profile.

Generally, a chromatographic profile for a specific molecule is unique and describes the physicochemical properties of that molecule. Parameters optionally used to characterize the chromatographic peak profile of a given molecule include the time of initial detection (liftoff), normalized slope, the time of inflection points relative to the time of the peak apex, the time of maximum response (peak apex), the peak width, at inflection points, at full-width-at-half-maximum (FWHM), peak shape asymmetry, and the time of the final detection (touch down) to name only a few.

FIG. 2B shows three related graphs that illustrate the collection of mass spectra during a period of time that covers an eluted peak of a precursor, according to one embodiment of the invention. A first graph 254 illustrates the alternating collection over elution time of low-energy spectra (i.e., spectra from unfragmented precursors, labeled "MS") and high-energy spectra (i.e., spectra from fragmented precursors, that is, product ions, labeled "$MS^E$".) Second and third graphs 254A, 254B respectively illustrate the MS and $MS^E$ spectral collection times and the reconstruction of the retention time peak associated with the precursor.

The reconstructed peak represents the chromatographic elution profile of a single precursor. The horizontal axis corresponds to elution time of the peak profile. The vertical axis corresponds to arbitrary units of intensity associated with the time-varying concentration of the precursor as it elutes from the chromatographic column.

An eluting precursor, passed to the mass spectrometer, thus produces ions in both low- and high-energy modes. The ions produced in the low-energy mode are primarily those of the precursor ions in possibly different isotopic and charge states. In proteomic studies, the precursor ions are peptides generated from enzymatic digestion (typically a tryptic digest) of the intact protein(s). In high-energy mode, the ions are primarily different isotopes and charge states of the fragment, or product, ions of those precursors. High-energy mode can also be referred to as elevated-energy mode.

In the graph 254, the alternating white and black bars thus represent the times at which spectra are collected with low and high-energy voltages of the eluting chromatographic peak. The low-energy graph 254A depicts the times at which a low-energy voltage is applied in the collision cell 218, resulting in low-energy spectra. The high-energy graph 254B depicts the times at which a high-energy voltage is applied in the collision cell 218, resulting in high-energy spectra.

The chromatographic peak of the precursor is thus sampled multiple times, by the high- and low-energy modes. From these multiple samples, accurate retention times of all the ions associated with the peak and seen in the high- and low-energy spectra can be inferred. These accurate retention times are obtained by interpolation of the intensities sampled by the respective spectra.

In following paragraphs and figures described below, reference is made to techniques described herein that may be used to combine spectra from multiple injections. Thus, an embodiment may produce an output spectrum as a result of processing performed with techniques described herein in which the output spectrum represents the result of combining input spectra from multiple injections.

Referring to FIG. 3, shown is a block diagram of processing that may be performed in an embodiment on an input data set 306 as may be obtained as a result of performing the method described in FIG. 1. The example 300 includes input data set 306 and selector 302 which are inputs to input data set processing 310. Processing 310 produces output data set 308. In one embodiment as described herein in more detail, the input data set 306 may include precursor and product ion data obtained using an LC/MS system for one or more injections which is then processed using a selected one of a variety of different retention time matching and product ion selection techniques in accordance with a value for the selector 302. An embodiment may include one or more such techniques for generating the output data set 308. In an embodiment including more than one such technique, a value for a selector 302 may be specified to select which one of the different techniques may be used to process the input data set 306. The processing 310 may use different rules or criteria in accordance with the selected technique to reduce or combine multiple spectra of precursor and product ion data into a single precursor and product ion spectrum as represented by output data set 308. As a result, the output data set 308 identifies those product ions determined as related to the single precursor as described in more detail elsewhere herein.

What will now be described are techniques that may be included in an embodiment and used in connection with performing retention time matching of precursors and selecting related product ions that are included in an input data set. A first retention time matching and product ion selection technique, which may be referred to herein as "Supertrack", is described in PCT International Publication No. WO 2006/133191 A2, PCT Patent Application No. PCT US2006/021919 ('919 PCT Publication), published on Dec. 14, 2006, METHODS AND APPARATUS FOR PERFORMING RETENTION-TIME MATCHING, Gorenstein et al., which is incorporated by reference herein. In an embodiment of Supertrack, the output data set for a given precursor includes a product ion if the product ion is included in two or more tracked spectra of the input data set. A tracked spectrum refers to a spectrum that is determined as including a selected precursor of interest. Different techniques for tracking a same precursor in multiple injections and corresponding spectra are described elsewhere herein.

A second retention time matching and product ion selection technique, which may be referred to herein as "Sumtrack", may perform a set UNION operation, or its logical equivalent in implementation, so that for a given precursor, the output data set includes a product ion if the product ion is included in at least one tracked spectra of the input data set. A third retention time matching and product ion selection technique, which may be referred to herein as "Hitrack", determines that, for a given precursor, the output data set includes the product ion spectrum associated with the spectrum of the input data set in which the precursor has the greatest intensity. In an embodiment in which the input data set includes 3 spectra, each of which is for a different injection and a same precursor is tracked in all 3 spectra, Hitrack selects the precursor and product ion spectrum of the 3 tracked spectra from the input data set in which the precursor is the most intense. The product ions in the selected spectrum which are retention time aligned with the precursor are included in the output data set. A fourth retention time matching and product ion selection technique, which may be referred to herein as "Mergetrack", may be characterized as using a combination of processing associated with Sumtrack and Hitrack. Embodiments of the last 3 foregoing techniques are described in more detail in following paragraphs. An embodiment may include any one or more of these techniques in any combination.

In following paragraphs, an embodiment of Sumtrack is first described followed by exemplary embodiments of the Mergetrack and Hitrack techniques. As will be appreciated by those skilled in the art, general discussion regarding retention time matching between precursor and product ions and tracking precursor ions across different injections as set forth in connection with Sumtrack is also applicable for use with other techniques performing retention time matching and product ion selection in combination with applying different rules to the input data set.

Each of the retention time and product ion selection techniques described herein use a set of product ion selection criteria to determine what product ions are related to a precursor. The criteria specify rules used in connection with selecting product ions determined as related to a precursor. All the techniques perform retention time matching between precursor and product ions. Additional criteria may be used that varies with the particular technique. An embodiment of the Sumtrack technique performs processing and determines that a product ion is related to a precursor if the product ion has a retention time that matches the precursor in at least one spectrum. An embodiment of the Sumtrack technique may use a set UNION operation, or its equivalent, in connection with the foregoing. An embodiment of the Hitrack technique may perform selection of a spectrum including the tracked precursor where the tracked precursor intensity is the greatest of all spectra including the tracked precursor. In connection with an embodiment of the Hitrack technique, each product ion in the selected spectrum having a retention time that matches the precursor is determined as related to the precursor. A first embodiment of the Mergetrack technique may use criteria of the Hitrack technique in determining a set of product ions related to a precursor. A second embodiment of the Mergetrack technique may use criteria of both the Sumtrack technique and the Hitrack technique in determining a set of product ions related to a precursor. It should be noted that the first and second embodiments of the Mergetrack techniques described herein result in selection of the same product ions and corresponding intensities for a precursor. However, both embodiments perform different processing to make the foregoing selection of related production ions for the precursor.

As described herein, precursors may be tracked across multiple injections. A same precursor may be identified in multiple injections in accordance with mass and retention time values for the precursor. Product ions produced as a result of fragmentation of the precursor will have substantially the same retention time as the precursor. Such product ions may be characterized as related to the precursor. In multiple injections, different product ions may appear as related to the same precursor. In connection with Sumtrack, a set UNION operation, or its equivalent, may be performed to collectively determine all product ions across multiple injections which are related to the precursor by having substantially the same retention time as the precursor. Thus, for Sumtrack, a product ion is included in the set of product ions related to the precursor if the product ion has substantially the same retention time as the precursor in one or more injections. For each such product ion related to the precursor, an intensity sum may be determined by adding the intensities of the related product ion across all the injections in which the related product ion appears.

It should be noted that in connection with the techniques herein, such as Sumtrack, in which data from multiple input spectra may be combined, an embodiment may include an intensity sum for a product ion in an output spectrum. As described elsewhere herein, two product ions in two different spectra may be determined to have the same mass if both product ions have a mass values within a given mass tolerance. The intensity sum for the product ion may be produced as a result of adding intensities of the product ion obtained from multiple input spectra provided each occurrence of the product ion in the multiple input spectra has a mass value within some mass tolerance. The mass of the product ion in the output spectrum may be determined by a rule, for example, such as by weighting the masses of the product ion in each input spectra by the respective intensities. Thus, an embodiment may produce an output spectrum including a product ion having an intensity sum by identifying occurrences of the product ion in the input spectra (by mass), replacing such occurrences with a single product ion in the output spectrum whose intensity is the sum of intensities of those identified occurrences, and assigning a mass value to the product ion in the output spectrum.

In an embodiment, the intensity sum may be used in connection with selecting the related product ions so that those product ions having the greatest intensity may be used in identification, discovery, and other applications of the techniques as described herein and known to those of ordinary skill in the art.

In connection with a sample or mixture, such as a complex protein sample including multiple proteins, many precursor ions may have a same retention time. When a precursor ion is fragmented, the product ions produced as a result of the fragmentation will also have the same retention time as that precursor. Due to the large number of precursor ions that may have the same retention time, product ions from different precursors may have substantially the same retention time. As a result, it may be difficult to match product ions to the respective, correct precursor ions. The matching of product ions to the appropriate precursor ion from which the product ions are generated has many applications as described herein and known to those skilled in the art.

In the context of LC/MS, a retention time matching and product ion selection technique, such as Sumtrack and others described herein, finds those product ions and the related precursor ion from which the product ions are derived having the same retention time and peak shape. The techniques described herein provide for association of product ions with precursors ensuring that product ions and precursors having substantially the same measured retention time are included in the output spectrum based upon retention time alignment.

The techniques for performing retention time matching and product ion selection may be used in connection with complex samples as well as simple samples. Complex samples may include, for example, a protein mixture as well as any one of a variety of different biological samples known in the art such as a serum, tissue, and cells. The retention time matching and product ion selection techniques may also be used in connection with a simple sample of a single polypeptide.

The techniques, such as Sumtrack and others described herein, for retention time matching of precursors to related product ions may be used, for example, in connection with the techniques described in the '919 PCT Publication to produce a polypeptide profile used in protein identification techniques. As described in the foregoing '919 PCT Publication, one or more profiles may be defined for one or more associated proteins in the sample. A protein profile is defined by values associated with retention time, ion mass, and ion intensity of precursor ions associated with the protein. Optionally, the profile of the protein is also defined by the identity of the protein. Some preferred embodiments include product-ion data in profiles. Thus, the profile of the protein may also be defined by values associated with retention time, ion mass, and ion intensity of product ions associated with the precursors of the protein. The profile may be stored in a catalog of profiles for later use in detecting, identifying and/or quantifying the protein in later analyzed subject samples. Optionally, the profiles are defined in an existing protein database by annotating the proteins listed in the database with values associated with retention time, ion mass, and ion intensity of precursor ions associated with the corresponding listed proteins.

In connection with such a profile for a protein as described herein, a set of precursor ions determined as the most intense precursors for the protein may be used to identify the protein. The profile may be used to detect, identify, track and/or quantify the protein to a sufficient specificity so that the protein may be distinguished from other proteins. The profile may also include additional information regarding each of the most intense precursors. The additional information may include, for example, one or more product ions associated with each of the precursors, and data (e.g., such as retention time, intensity and/or mass or m/z) about each of the one or more product ions. The retention time matching and product ion selection techniques may be used to identify the product ions associated with the most intense precursors as included in the profile. Information from the profile, such as the mass of the most intense precursor ions along with the masses of a sufficient number of its product ions, can identify the sequence of the protein to a high degree of confidence.

The techniques herein, such as Sumtrack and others, described in following paragraphs may be used to detect, identify, track and/or quantify peptides and proteins and addressing problems in proteomics. The techniques described herein may also be used in connection with samples or mixtures that may be characterized as other than biological. In connection with proteomic applications, the peptides may result from enzymatic digestion of sample proteins. Reliable identification of peptide precursors allows identification and quantitation of sample proteins.

The retention time matching and product ion selection techniques described herein may be used to reliably assign or match product ions to precursors in a deterministic manner without utilizing other methodologies, such as statistical methods, to compensate for incorrect matching of product ions and precursors. The precursors and related product ions identified using the techniques herein may be stored in a database alone, or in connection with other data such as when annotating an existing data store. A data store may be characterized as any one of a variety of different data containers used to store data. Examples may include, but are not limited to, a database, one or more files, directories, and the like. The catalog containing protein profiles as described herein may be implemented using any one or more of the foregoing.

Although reference in illustrative examples herein may be made to applications using protein digests analyzed using the foregoing technique described in Bateman (U.S. Pat. No. 6,717,130, which is incorporated by reference herein), an embodiment may produce data sets as illustrated generally in FIG. 1 using other methodologies known in the art such as, for example, data dependent analysis or acquisition (DDA) used to isolate selected precursor ions and identify product ions for the selected isolated precursor. In one embodiment, a mass spectrometer may be used to perform DDA in which the mass spectrometer includes a collision cell and a quadrupole. When operating in accordance with the DDA technique, the quadrupole is used as a filter in a first phase to selectively isolate and select only precursors of interest. Thus, only selected precursors are produced as an output of the first filtering phase. The selected precursors are then passed to a collision cell where they are fragmented, as using a sufficiently high voltage, to generate fragments or product ions and obtain a desired number of scans for the isolated precursor and product ions. The foregoing DDA technique may be repeated for isolating different precursors and obtaining a desired number of scans for the precursors and related product ions.

In connection with any of the retention time matching and product ion selection techniques described herein, an embodiment may determine masses of particular precursors of interest using a variety of different techniques. For example, in one embodiment utilizing the Bateman techniques as described elsewhere herein, the low energy (LE) cycle or mode may be used to generate spectra including one or more precursor ions. Other techniques used to generate the input data set, such as the DDA technique, may also be used to isolate precursors and determine their particular masses. The selected precursors and associated masses may be subsequently identified in the input data set.

In an embodiment using the techniques herein, mass spectra as produced from different experiments using a mass spectrometer may be compared. The retention time matching and product ion selection techniques described herein may include the mass spectra in an input data set, and may combine information regarding precursor and related product ions of the foregoing mass spectra using a set union operation as will be described in more detail in following paragraphs. The mass spectra may include data for multiple precursors. For simplicity of illustration and explanation, examples are described herein in which the mass spectra may include data related to a single precursor and product ions having substantially the same measured retention time and peak shape as the precursor. However, the product ions have different mass or m/z values. The retention time of the single precursor and its related product ions in each of the different spectra may be within an expected retention time window of error incurred due to possible measurement error. In one embodiment, the window of error may be within a threshold of $1/10^{th}$ of a peak width of the retention time of the precursor as determined using the full width half maximum (FWHM) methodology. As known in the art, FWHM is determined as the distance between two points on either side of the chromatographic peak at which the curve reaches half its maximum value. An embodiment may also use other values as the foregoing window of expected error in accordance with the expected error of system and methodologies utilized in an embodiment.

The mass spectra included in the data set may include precursors in multiple injections each having a retention time within a retention time tolerance window (as will also be described in more detail in following paragraphs). Each of the mass spectra may then be aligned or normalized in accordance with a single retention time. For example, the mass spectra in the data set may include those mass spectra having a precursor with a retention time of several chromatographic FWHM of the precursor in another mass spectrum. Each of the spectrum in the data set may then be aligned at a single retention time, such as "n". In the alignment process, each precursor ion in a spectrum is shifted by a quantity and in a direction to align the precursor at a retention time of "n". Additionally, the product ions of the spectrum are also shifted by the same quantity and in the same direction in accordance with the shift of the precursor of the spectrum. The foregoing alignment is repeated for each of the spectrum. After alignment, each spectrum may be examined. If a product ion in the spectrum has a retention time that falls within a window of error with respect to the precursor retention time "n", of $1/10^{th}$ the chromatographic peak width (e.g., "n"+/−$1/10^{th}$ the chromatographic FWMH of the chromatographic peak associated with the ion), then that product ion is determined to also have the same retention time "n" as the precursor and is matched with the precursor. In contrast, if the retention time of the product ion is not within the window of error, the product ion is determined to not be a match for the precursor in that particular spectrum. Once all spectra have been processed, the rules associated with one or more the different retention time matching and product ion selection techniques herein may be applied.

The data set used with the retention time matching and product ion selection techniques herein may include spectra, such as MS spectra, generated using a variety of different techniques. For example, the spectra may be obtained using an LC/MS analysis of complex mixtures using the techniques of Bateman or the DDA technique. The data set may also be obtained from MALDI-MS-MS, and using spectrometers with high or low resolution.

The product ions included in a data set for use in connection with the retention time matching and product ion selection techniques may be produced using a variety of different methodologies known in the art. The product ions may be produced using any one of a variety of different fragmentation techniques. An embodiment may use a mass spectrometric (MS) methodology as described in Bateman using a high- and low-energy switching protocol applied as part of an LC/MS analysis of a single injection of a peptide mixture. In such data the low-energy (LE) spectra contains ions primarily from unfragmented precursors, while the high-energy (HE) spectra contain ions primarily from fragmented precursors or product ions.

Each spectrum in the data set to which the retention time matching and product ion selection techniques described herein are applied may be obtained from an independent analysis or experiment. For example, in an LC/MS context, each of the M spectra included in an input data set may be obtained from M different injections. These M injections may be from M injections of the same aliquot (e.g., replicate injections). Alternatively, each of the M injections may use a different sample mixture. An embodiment may also utilize a data set in which the spectra are produced from some number of replicate injections of some number of different sample mixtures.

In the context of LC/MS, the retention time matching and product ion selection techniques find those product ions and the related precursor ion from which the product ions are derived having the same retention time and peak shape. All of the retention time matching and product ion selection techniques described herein provide for association of product ions with precursors ensuring that product ions and precursors having substantially the same measured retention time are included in the output spectrum based upon retention time alignment with respect to the precursor.

The retention time matching and product ion selection techniques herein depend on the principle that product ions maintain strict association with the precursor ion from which the product ions are derived. This association may manifest itself by both the product ions and the precursor ion appearing at substantially the same measured retention time. The retention matching techniques take advantage of the fact that ions which are unrelated to a selected precursor will not maintain the foregoing association for the spectra analyzed in the input data set.

In connection with any of the techniques herein, two precursor ions in different injections may be determined to be instances of the same precursor in different injections if their masses lie within a predetermined mass tolerance window and both have retention times occurring within some retention time tolerance. Two product ions appearing in different injections and having masses with a predetermined mass tolerance window may be determined to be an instance of the same product ion. Two ions may be deemed to have a same mass if a first mass of the first ion is within a predetermined mass tolerance of a second mass of the second ion. This mass tolerance may be used in connection with the techniques described herein with respect to precursor ions as well as product ions. In one embodiment, the mass tolerance may be +/−$1/10^{th}$ of the FWHM of the mass spectral peak as may be included in a mass spectrum expressed in parts-per-million (PPM). Other mass tolerances may be used in connection with, and may vary with, an embodiment.

A precursor and a product ion are deemed to be related if each have a same retention time as determined in accordance with the error window size or retention time window as described elsewhere herein. In an embodiment, the error window size or retention time window used in connection with matching a precursor with a product ion, may be related to the chromatographic FWHM of the mass spectral peaks, or other tolerance as related to the resolution of the instrument, such as the MS instrument used to obtain the spectra in the input data set.

As a result of using one of the retention time matching and product ion selection techniques described herein, such as Sumtrack, an output spectrum may be produced which includes those product ions deemed to be related to a precursor ion.

The techniques described herein may utilize an input data set including as few as two input spectra. Each of the input spectra may include a precursor of interest and as few as a single product ion associated with the precursor of interest. The intensity sum determined for each product ion determined as related to the precursor of interest as a result of performing one of the techniques herein may be used to further rank the related product ions and determine a relevance strength or degree of certainty to which each product ion is related to the precursor. In one embodiment, the larger the intensity sum for a product ion, the more relevant the product ion to the precursor.

In addition to spectra, an input data set used in connection with the techniques described herein may include ions in an ion list. An ion list may be obtained, for example, from three-dimensional data such as may be acquired utilizing LC/MS or other experimentation and processing methodologies. Each ion included in an ion list may be annotated by the ion's retention time, mass or m/z, and/or intensity. In such instances where three-dimensional data is utilized, spectra may be obtained, for example using retention time binning as described, for example, in Plumb et al, US patent publication No. 2005/0127287, filed on Nov. 16, 2004, METHOD OF USING DATA BINNING IN THE ANALYSIS OF CHROMATOGRAPHY/SPECTROMETRY DATA, which is incorporated by reference herein, or PCT International Publication No. WO 2005/079263 A2, PCT Patent Application No. PCT US2005/004180, published on Sep. 1, 2005, APPARATUS AND METHOD FOR IDENTIFYING PEAKS IN LIQUID CHROMATOGRAPHY/MASS SPECTROMETRY DATA AND FOR FORMING SPECTRA AND CHROMATOGRAMS, Gorenstein et al which is incorporated by reference herein.

In connection with the techniques described herein, multiple precursors having a same retention time in one injection are found to have slightly different retention times in other injections even under replicate conditions, for example, as may be determined utilizing the Bateman technique. Accordingly, product ions associated with multiple precursors may have a single retention time in the first injection and the multiple precursors may have slightly but measurably different retention times in other injections. As a result, the product ions that may have a first retention time in a first injection may have a slightly different retention time in a subsequent injection even under replicate conditions. The techniques described herein advantageously utilize the fact that as long as the difference in measured retention time between the precursor and the product ions are within the specified retention time window of error or threshold, then the product ions may be associated with the precursor.

It should be noted that the techniques herein compare mass values of spectral peaks within the input data set or spectrum. No prior knowledge regarding mass values or m/z values for the precursor and/or product ions is needed. Additionally, no prior knowledge of the sequence for a given protein is needed to utilize the techniques described herein on a sample although the techniques described herein may be used to further annotate a database or catalog.

In connection with Sumtrack, an embodiment may use the set UNION operation, or its equivalent, with respect to all product ions determined as a match for a precursor tracked across multiple injections. Thus, if the product ion is determined as a match with respect to the precursor retention time "n" in at least one injection having a corresponding spectrum, then that product ion is included in the resulting set formed with the UNION operation. As such, the retention time matching of precursor and related product ions may be performed in a deterministic, reliable manner. The resulting set formed may be included in an output spectrum containing the precursor and all identified related (e.g., matched) product ions from the mass spectra of the input data set.

An embodiment of the Sumtrack technique for retention time matching using the set UNION operation, or its equivalent, may be applied to M spectra in which each of the M spectra include a same precursor and a set of one or more product ions related to the precursor (e.g., product ion and precursor in a same spectrum are within the retention time window of error). The precursor may be tracked across the M spectra and a precursor in one spectrum may be determined as a match for (e.g., the same as) a precursor in another spectrum in accordance with one or more criteria (e.g., substantially the same retention time, mass, and the like) as described elsewhere in more detail. A product ion may be included in the output spectrum if it appears in any one or more of the M spectra and is within the retention time window of error with respect to the precursor's retention time. Thus, the output spectrum includes the set UNION of all product ions associated with the precursor across the M spectra. Additionally, an intensity sum may be associated with each product ion. The intensity sum of a product ion may be determined by adding the intensities of the product ion across the M spectra. An intensity is obtained for each of the M spectra in which the product ion is included and is determined as related to the precursor, and all such intensities are summed to produce the intensity sum for the product ion. As noted elsewhere herein, two product ions in different spectra may be deemed the same product ion if both have the same mass within a specified mass tolerance.

An embodiment of Sumtrack as described for matching precursor and product ions across multiple injections of an input data set may be applied to a variety of different areas and used in connection with a variety of different methodologies. For example, these techniques may be used in proteomics and small molecule studies. These techniques may be used to detect precursor and related product ions in replicate injections of a sample and the storage of such information in the database, such as an annotated peptide catalog and included in a peptide profile. Such stored information may be extracted from a data store for comparison against characteristics of unknown samples. Such stored information may be used to detect, identify, and/or quantify an unknown sample. The foregoing uses also are applicable to the other retention time matching and product ion selection techniques described herein.

Using Sumtrack, a set UNION operation may be applied to the product ions associated with the precursor across multiple injections and the resulting set UNION of such product ions may be determined as related to the precursor. Thus, use of Sumtrack, as well as others of the foregoing techniques for retention time matching and product ion selection provide for separating product ions which are related from those which are unrelated with respect to a precursor. With Sumtrack, for each such product ion in the set UNION, an intensity sum may be determined by adding the intensities for the product ion related to the precursor across the multiple injections. An intensity sum may also be determined for the precursor by similarly adding the intensities for the precursor across the multiple injections.

The output produced as a result of the techniques described herein may be in the form of a spectrum. With Sumtrack, the output spectrum may include the precursor and the one or more related product ions included as a result of determining the set UNION of product ions across multiple injections. The resulting output spectrum may be stored, displayed, used in connection with searching to identify an unknown peptide, retention time tracked, and the like.

Figure 4:
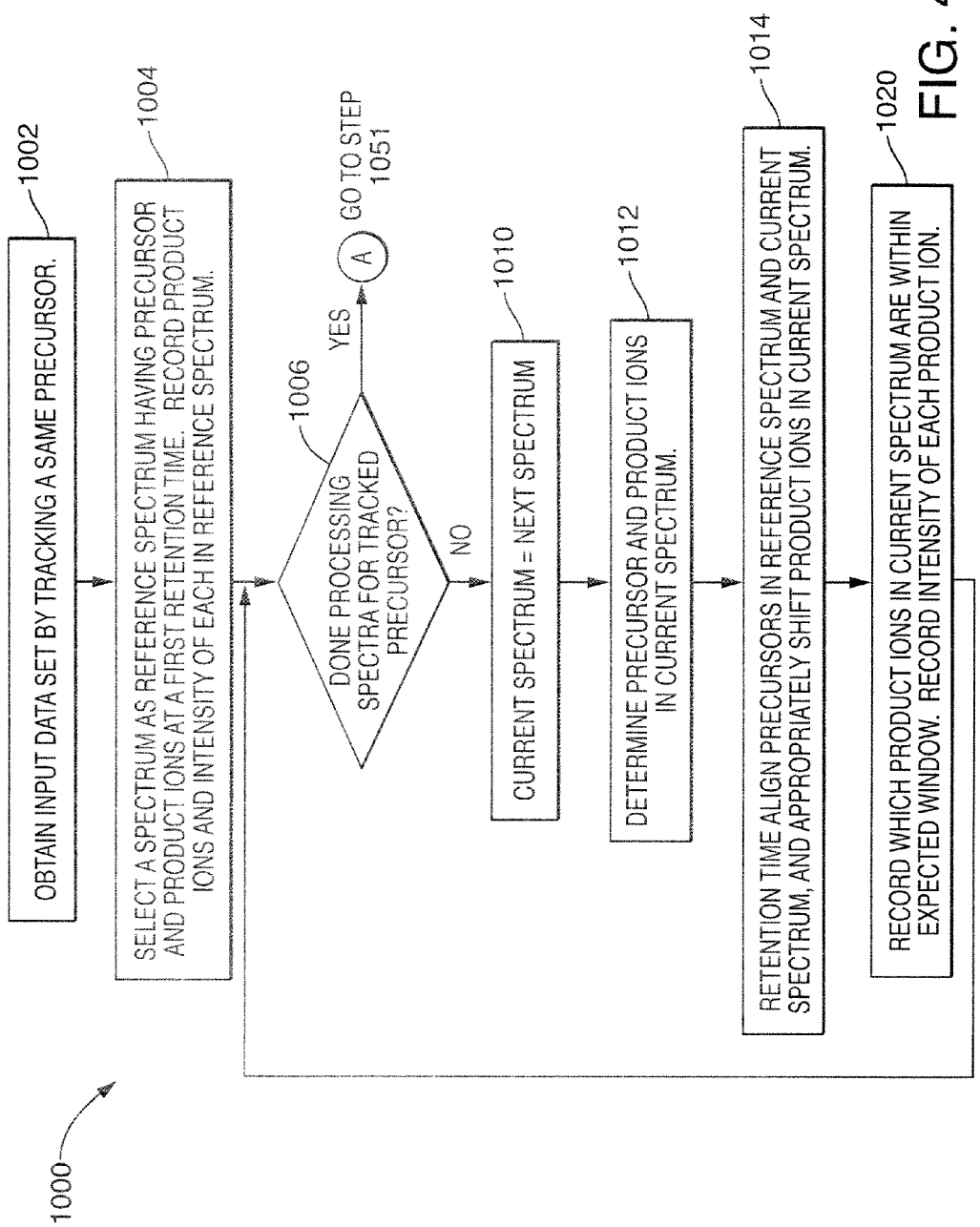
FIG. 4 and FIG. 5 are flow diagrams of processing steps that relate to retention time matching of a precursor and its related product ions using a first technique, Sumtrack, described herein in accordance with one embodiment of the invention.
Figure 5:
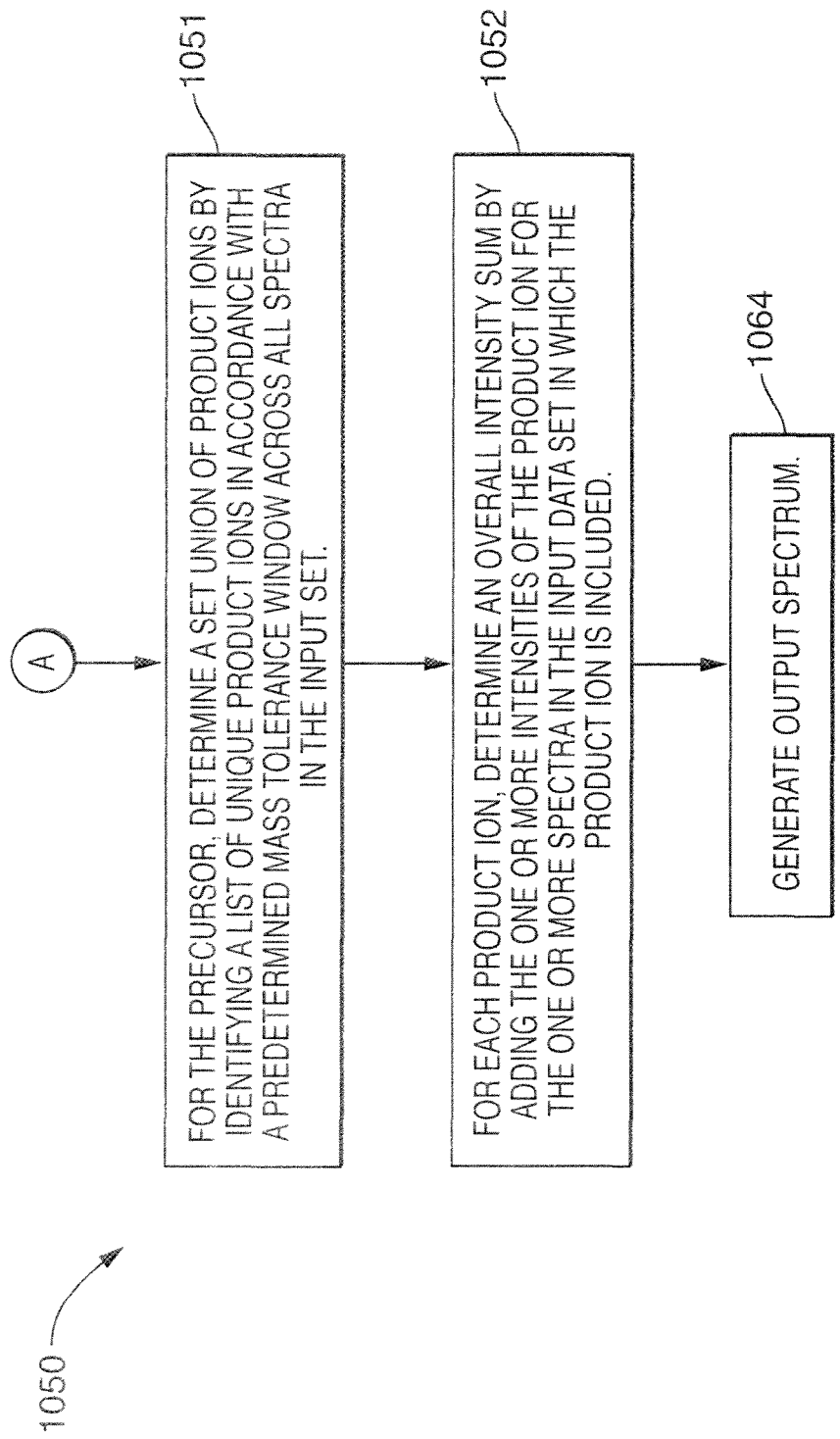

Referring now to FIGS. 4 and 5, shown are flowcharts of processing steps that may be used in an embodiment in connection with performing retention time matching of a precursor and selecting its related product ions using Sumtrack. The steps of FIGS. 4 and 5 summarize processing just described.

At step 1002, an input data set is obtained. The input data set may include data from multiple injections, and may be in any one or more of a variety of different forms including ion lists and spectra although spectra are included in the steps of flowcharts 1000 and 1050 for illustration. The input data set used in connection with FIGS. 4 and 5 includes spectra for a tracked precursor so that each spectrum of the input data set includes a same precursor. The input data set used in connection with FIGS. 4 and 5 processing steps may be generated from an original data set by selecting a precursor and determining which spectra of the original data set include the selected precursor. An embodiment may alternatively determine which spectra include the selected precursor at different processing points than as illustrated in this particular embodiment. Tracking precursors between multiple injections may be performed using the technique described in PCT Patent Application International Publication No. WO 2005/079261 A2, PCT patent application no. PCT/US2005/004176, published on Sep. 1, 2005, SYSTEM AND METHOD FOR TRACKING AND QUANTITATING CHEMICAL ENTITIES, Gorenstein et al., which is incorporated by reference herein, in which first and second precursors in different injections are determined to be the same if the first precursor's mass is within a particular mass tolerance of the second precursor's mass, and if the first precursor's retention time is within the second threshold or window of the second precursor. This is described in more detail elsewhere herein.

At step 1004, a spectrum of the input data set is selected. The spectrum selected in step 1004 may be referred to as the reference spectrum. The injection which was used in obtaining the reference spectrum may be referred to herein as the reference injection. A precursor having a first retention time in the reference spectrum is determined. In one embodiment, one or more precursors may be determined as those ions having the greatest mass and intensity. For purposes of illustration in connection with the flowcharts 1000 and 1050, it is assumed that only a single precursor is included in each spectrum of the input data set. As described herein, such as in connection with the Bateman technique, different methodologies may be utilized to determine the mass of a selected precursor of interest. With reference to the Bateman technique, masses of precursors may be determined by examining the resulting spectra produced using a LE scan.

In the reference spectrum, the product ions having a retention time that is within the retention time window with respect to the retention time of the precursor may be characterized as product ions related to the precursor. The related product ions and associated intensities may be recorded as part of step 1004. Using the techniques herein, the foregoing is performed for the precursor tracked across multiple spectra. As described below in more detail, a single spectrum including the tracked precursor is processed with an iteration of the loop formed in steps 1006, 1010, 1012, 1014 and 1020. All product ions determined as related to the precursor in the one or more spectra are then combined such as using a set UNION operation in subsequent processing steps. The resulting set of product ions are determined as matched or associated with the precursor ion.

In connection with step 1004 when determining the product ions of the reference injection occurring at the same retention time as a precursor of the reference injection, all product ions occurring within the retention time window or error window of the precursor's retention time are considered. For example, a precursor may have a retention time of T1 in the reference injection. A first product ion may have a retention time which falls within T1 and T1+/− the retention time window. The first product ion is included in the set UNION and considered as a product ion associated with the precursor. If the first product ion has a measured retention time which is outside the range of T1+/− the retention time window, then the first product ion is not considered as related to the precursor for that injection. The foregoing retention time window is also used in subsequent processing steps of each iteration of the loop formed in FIG. 4 as noted above in connection with matching product ions to precursors in target injections. A target injection may refer to an injection of the input data other than the reference injection. Target injections may be used in producing the remaining spectra processed in the flowchart 1000 in the loop formed with a top testing step 1006.

At step 1006, a determination is made as to whether all the spectra in the input data set including the tracked spectra have been processed. If not, control proceeds to step 1010 where the variable current spectrum is assigned to the next spectrum in the input data set. At step 1012, the precursor and product ions for the current spectrum are determined. The current spectrum is searched for an ion having the same mass and retention time (within a second threshold or window representing a retention time tolerance) as the precursor of the reference spectrum. It should be noted that one or more of the product ions present in the reference spectrum may also appear in the current spectrum. There may also be product ions which are present in only one of the reference spectrum and the current spectrum.

An embodiment may utilize the foregoing second threshold or window representing a window of time used when searching for a precursor having a particular mass in a target injection such as in steps 1012 and 1002 for processing to track the precursor in the reference and target injection. For example, a precursor having a mass m1 at a retention time T1 may be determined in a reference injection. For a subsequent target injection, processing searches for an ion having the same mass m1 and a retention time of T1+/− the second threshold or window. The second threshold or window may be empirically determined and may vary in accordance with an embodiment. For example, an embodiment may assign an initial value to the second threshold, such as based on 2-3 chromatographic peaks widths. The second threshold may be modified or refined in accordance with empirical experimentation of a system. For example, if an embodiment utilizes a system or methodology introducing a large amount of error or noise, the second threshold or window may be increased.

In connection with step 1012 processing, it should also be noted that a precursor in the current spectrum is identified as being at a mass and is matched to the precursor in the reference spectrum of step 1004 having the same mass. A first mass of the precursor in the reference spectrum may be deemed to be the same mass as a second mass of a precursor in the current spectrum if the first mass is within the specified mass tolerance of the second mass. In the exemplary embodiment illustrated for simplicity of description, each spectrum processed includes only a single precursor of interest so that once the single precursor is identified, the remaining ions may be identified as product ions.

At step 1014, the precursor of the current spectrum may be time-aligned with the precursor of the reference spectrum and all product ions in the current spectrum are appropriately and accordingly time shifted. For example, if the retention time of the precursor in the reference spectrum is 10.0 minutes and the retention time of the precursor in the current spectrum is 9.8 minutes, the precursor and product ions in the current spectrum are shifted +0.2 minutes. Once the shifting is complete, control proceeds to step 1020 where the product ions in the current spectrum which are within the expected retention time window are determined. At step 1020, the particular product ions which are within the retention time window may be recorded for use in a later processing step. Additionally, the intensity of each product ion in the current spectrum within the retention time window (e.g., related to the precursor in the current spectrum) is recorded for use in connection with subsequent processing steps in determining the intensity sum. Control then proceeds from step 1020 to step 1006.

If the determination at step 1006 evaluates to yes, control proceeds to step 1051. In step 1051, a list of unique product ions in accordance with the predetermined mass tolerance window is determined. The product ions included in the reference spectrum and subsequent spectrum of the input data set as determined at step 1020 are examined. A first product ion in one spectrum having a first mass may be deemed as having a same mass as another product ion in a second spectrum if the first mass and the second mass are within the predetermined mass tolerance window. In connection with the techniques described herein, the first and second product ions may be deemed to be the same product ion in two different spectra. From step 1051, control proceeds to step 1052. For each product ion as determined in step 1051, an overall intensity sum is determined by adding the one or more intensities of the product ion, respectively, for the one or more spectra in the input data set in which the related product ion is included. It should be noted that an embodiment may also sum the intensities of the precursor across the spectra of the input data set to determine an intensity sum for the precursor.

In accordance with techniques described herein, step 1051 results in determining, across the input data set, a set of all product ions having substantially the same retention time as the precursor (e.g., within the retention time window of error). A product ion is included in this set by performing the set UNION operation, or its equivalent, so that if the product ion is within the retention time window of the precursor for at least one spectrum in the input data set, the product ion is determined as related to the precursor. Control proceeds to step 1064 to generate an output spectrum. As described elsewhere herein, the output produced may be in a form other than a spectrum, such as an ion list. The output spectrum or other output generated in step 1064 may include the product ions determined to be associated with the precursor by having substantially the same retention time and peak shape as the precursor. The product ions, alone or in conjunction with the precursor, may be included in the output spectrum along with an indication of the associated intensity sums.

The Sumtrack technique described herein will now be illustrated with additional figures. For the sake of simplicity of illustration, only a single precursor is illustrated although the techniques described herein may be used in connection with samples having multiple precursors and their associated product ions.

Figure 6:
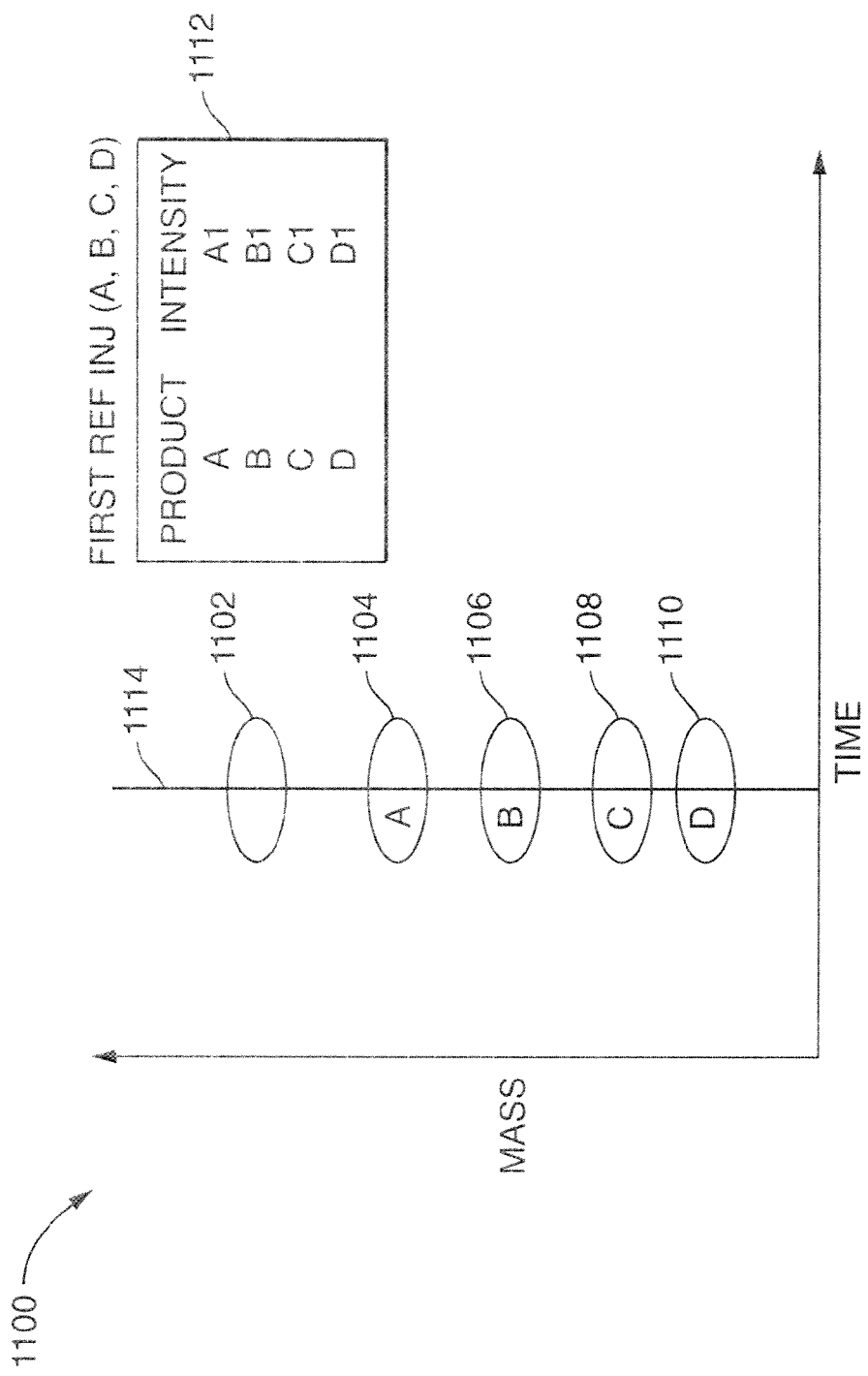
FIGS. 6-11B are graphical representations of injections illustrating use of the first technique herein in accordance with one embodiment of the invention.

Referring now to FIG. 6, shown is a graphical representation of a reference injection. In this example 1100, a precursor 1102 and product ions 1104, 1106, 1108, and 1110 have the retention time of the precursor 1102 as indicated by 1114. It should be noted that all product ions having a measured retention time within the retention time window are considered. Table 1112 includes a list of intensities associated with the different product ions of the reference injection illustrated.

Figure 7:
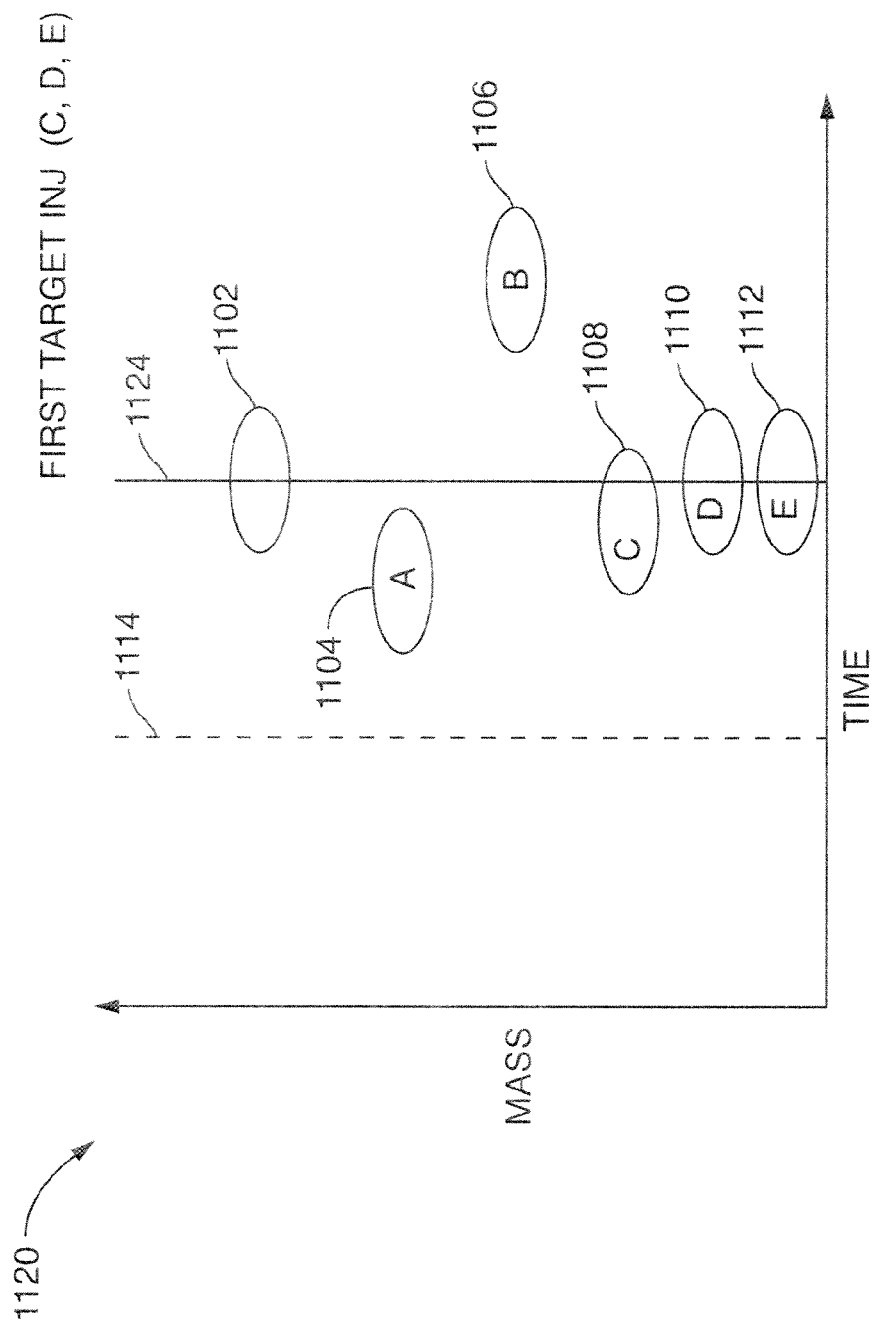
Figure 8:
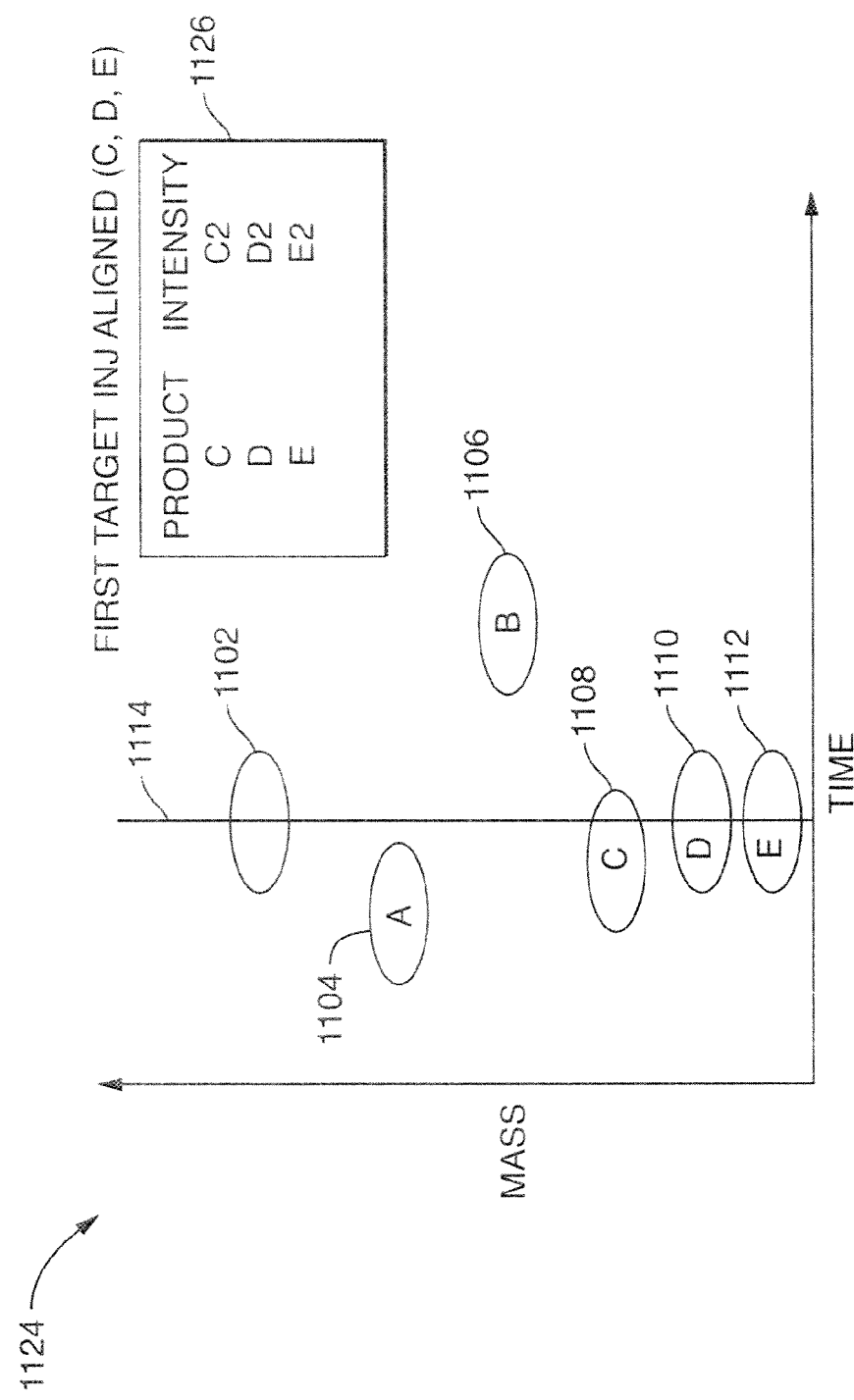

Referring now to FIG. 7, shown is a graphical representation of another injection. The injection of the example 1120 may be referred to as a first target injection including precursor 1102 and product ions 1104, 1106, 1108, 1110 and 1112. In this example 1120, the data for the target injection is searched for a retention time for the same mass as the precursor 1102 from the reference injection. The search for the retention time is performed with respect to the second threshold or retention time tolerance as described above for use when tracking a same precursor in different injections. An embodiment may use a technique such as that described in International Publication No. WO 2005/079261 A2 mentioned above for tracking precursors among multiple injections. In the example 1120, the precursor 1102 is illustrated as having a retention time indicated by 1124. In FIG. 8, shown is the alignment or normalization of the first target injection in accordance with the retention time of the precursor from the reference injection. The precursor from the reference injection and the first target injection are aligned. The product ions are also accordingly shifted. It should be noted that as described for the reference injection, the precursor of a target injection may be determined as those one or more ions having the greatest mass and intensity. In connection with the example 1124, note that product ions 1104 and 1106 do not have the same retention time of 1114 as the precursor as may be determined with respect to the retention time window described above that may be used when determining which precursor and product ions have substantially the same retention time. The remaining product ions 1108, 1110 and 1112 have the retention time 1114 within the expected retention time window. Table 1126 lists the intensities associated with the product ions illustrated in the example 1124.

In the example 1124, note that product ions 1104 and 1106 are illustrated as not having the retention time 1114 within a retention time window as may be determined, for example, using $+/-\frac{1}{10}^{th}$ the FWHM of the mass spectral peak as described elsewhere herein.

Figure 9:
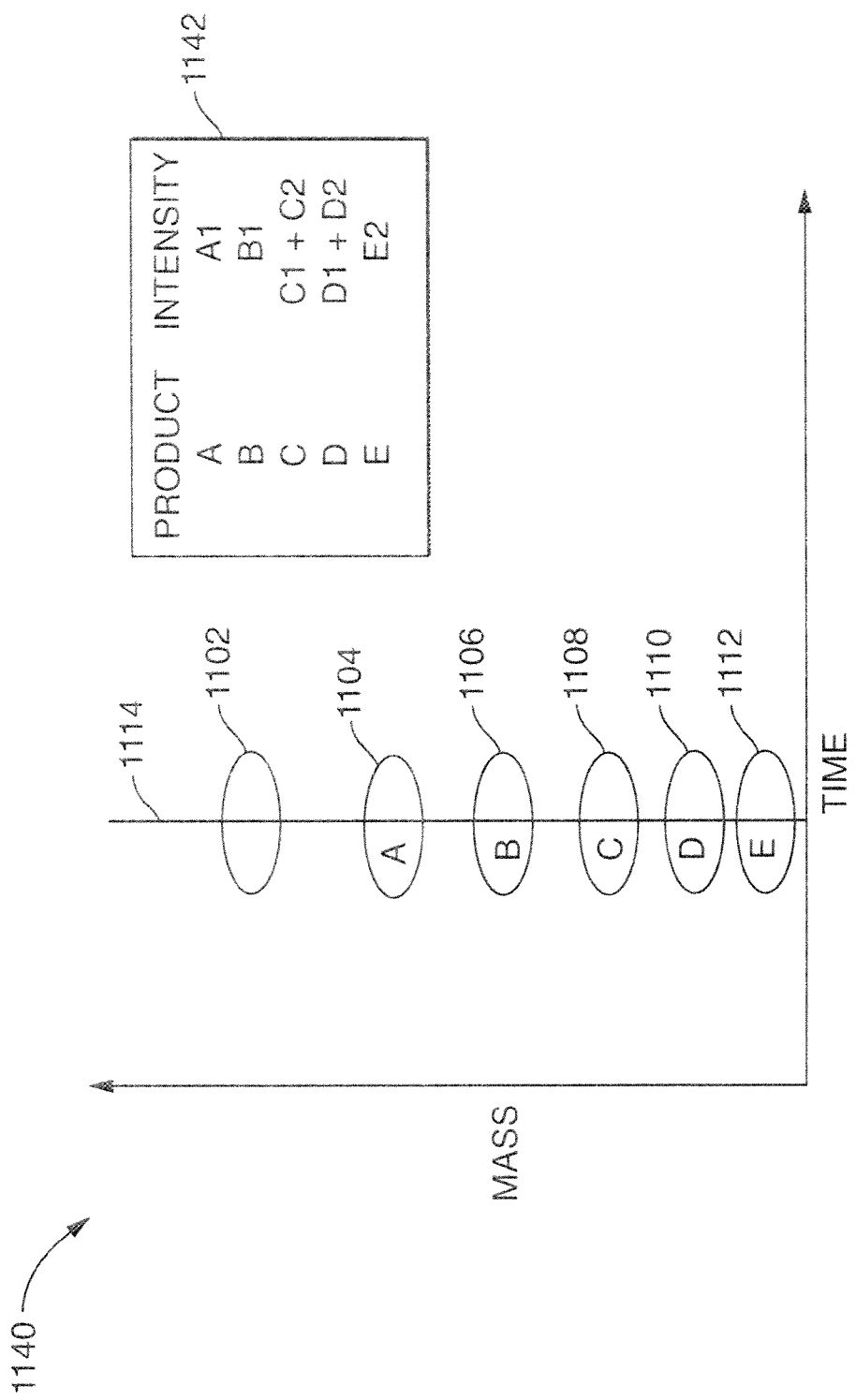

An example of an output spectrum including the precursor and associated product ions as determined using the techniques described herein using the Sumtrack technique which applies the set UNION operation is illustrated in FIG. 9. Using the Sumtrack technique herein, the set UNION operation is applied to the product ions determined as related to the precursor in the reference injection (e.g., FIG. 6) and the product ions determined as related to the precursor in the first target injection (e.g., FIGS. 7 and 8):

product ions of reference injection related to precursor {A, B, C, D} UNION product ions of first target injection related to precursor {C, D, E}={A, B, C, D, E}

Based on the foregoing examples, it may be determined that product ions 1104, 1106, 1108, 1110 and 1112 are matched or associated with the precursor ion 1102 having a retention time illustrated by 1114.

Additionally, table 1142 shows a table of intensity sums for the product ions determined by summing the intensities for each product ion across the spectra including each related product ion. Table 1142 sums the intensities from table 1126 of FIG. 8 and table 1112 of FIG. 6. Although not illustrated, the intensity associated with the precursor 1114 may be the sum of the intensity of the precursor in the reference and target injection.

The foregoing Sumtrack technique for performing retention time matching and product ion selection may be used to annotate a database or catalog, such as a peptide catalog. As known in the art, for example, a protein sequence database may be initially obtained and stored on a data storage device. The database may be annotated using the techniques just described. The peptide database includes information such as what ions comprise a particular peptide. The techniques described herein may be used to annotate the database to further identify which of the ions of those listed in the database are used in connection with protein profiling, for example, to characterize or identify the protein. For example, there may be a peptide database which includes a protein and identifies the 20 tryptic peptides in the protein's sequence. It may be that only a portion, such as for example 10, of those 20 peptides are ionized and may be used as precursors to identify the protein. Using the techniques described herein, the peptide database may be annotated to denote the three most intense precursors of the 10. The three most intense precursors may be used to identify the protein as in connection with profiling as described elsewhere herein. The peptide database may be further annotated to identify the product ions for each of the precursors as also identified, for example, using one information produced as a result of performing one of the retention time matching and product ion selection techniques described herein.

In connection with an input data set in which a single spectrum has more than one precursor with a same retention time, a reference injection may be determined. Such a spectrum may be produced, for example, in connection with an analyzed complex sample. The mass of each precursor may be determined from the reference injection. As an example, let a first mass, m1, be associated with a first precursor and a second mass, m2, be associated with a second precursor. Multiple target injections may be examined with respect to each precursor. The target injections may be searched for an ion having the mass m1 and having a retention time within the specified second threshold representing a retention time tolerance used when tracking precursors in different injections. Such an ion is determined to be the first precursor in the target injection. A retention time for the first precursor in a target injection is determined and aligned with the retention time of the first precursor in the reference injection. Alignment and other processing steps may be performed as described herein for each of the target injections to determine which product ions are associated or matched with the first precursor. The same set of target injections may also be processed with respect to the second precursor having mass m2. In a manner similar to that as set forth regarding the first precursor with mass m1, the target injections may be searched for an ion having the mass m2 and having a retention time within the second threshold as described elsewhere herein. A retention time for the second precursor in a target injection is determined and aligned with the retention time of the second precursor in the reference injection. Alignment and other processing steps may be performed as described herein for each of the target injections to determine which product ions are associated or matched with the second precursor. As such, in each of the target injections, appropriate product ions occurring at substantially the same retention time as each of the precursors may be examined and processed.

To further illustrate the use of the Sumtrack technique with a spectrum including more than one precursor, reference will be made to FIGS. 10, 11A and 11B.

Figure 10:
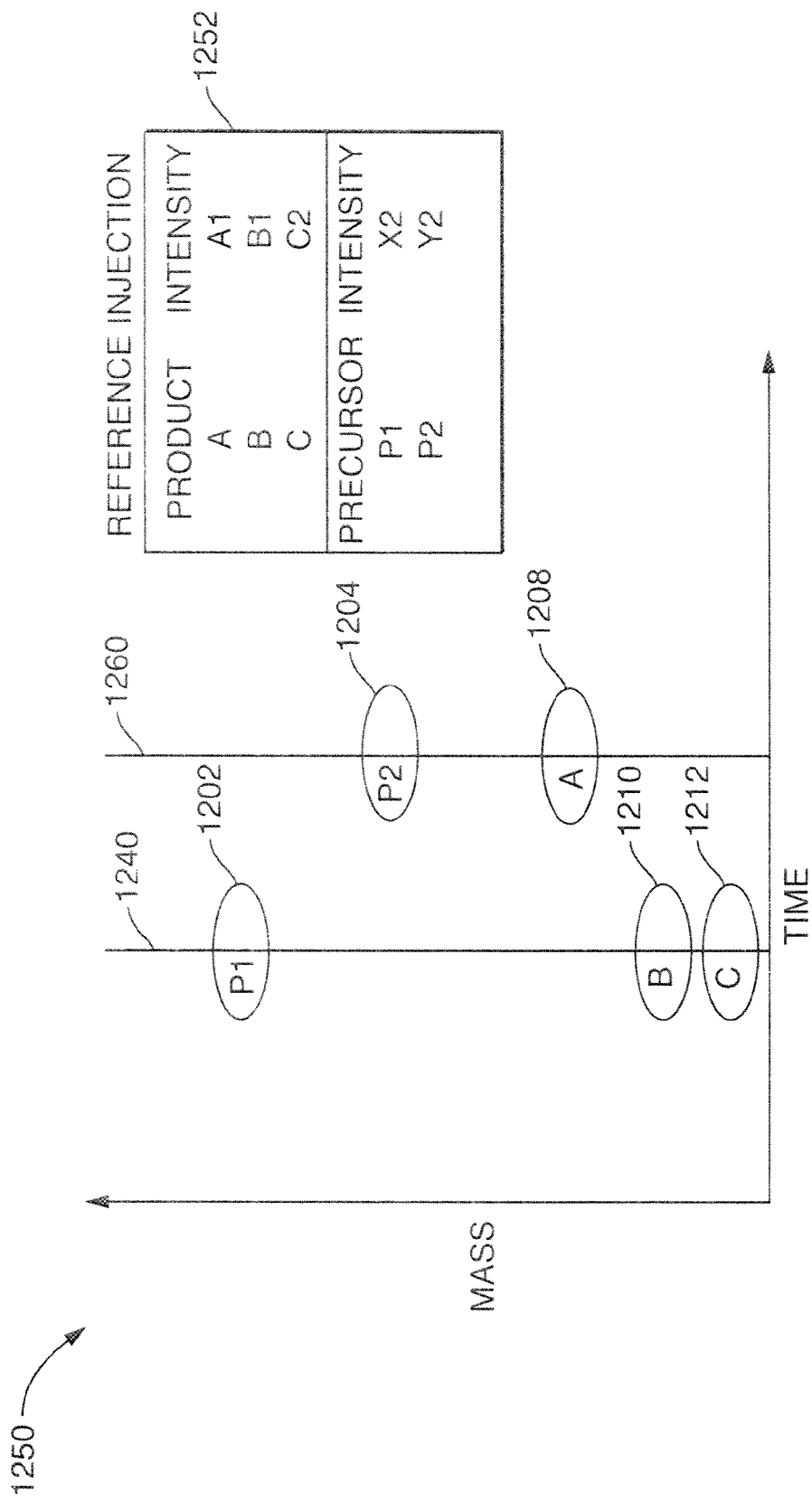

Referring to FIG. 10, shown is an example spectrum that may be produced for a reference injection. In the example 1250, it may be determined that elements 1202 and 1204 are precursors. Elements 1202 and 1204 may represent ions determined to be precursors in accordance with their large mass and intensity in relation to other ions 1208, 1210 and 1212. Precursor 1202 may have a retention time of 1240 and precursor 1204 may have a retention time of 1260. Table 1252 illustrates the intensities associated with the products and precursors in the spectrum of 1250. In the reference injection, product ions 1210 and 1212 are determined as related to precursor 1202 (e.g., within the retention time window of 1240 used for determining related product ions having substantially the same retention time as the precursor 1202). Product ion 1208 is determined as related to precursor 1204.

Figure 11A:
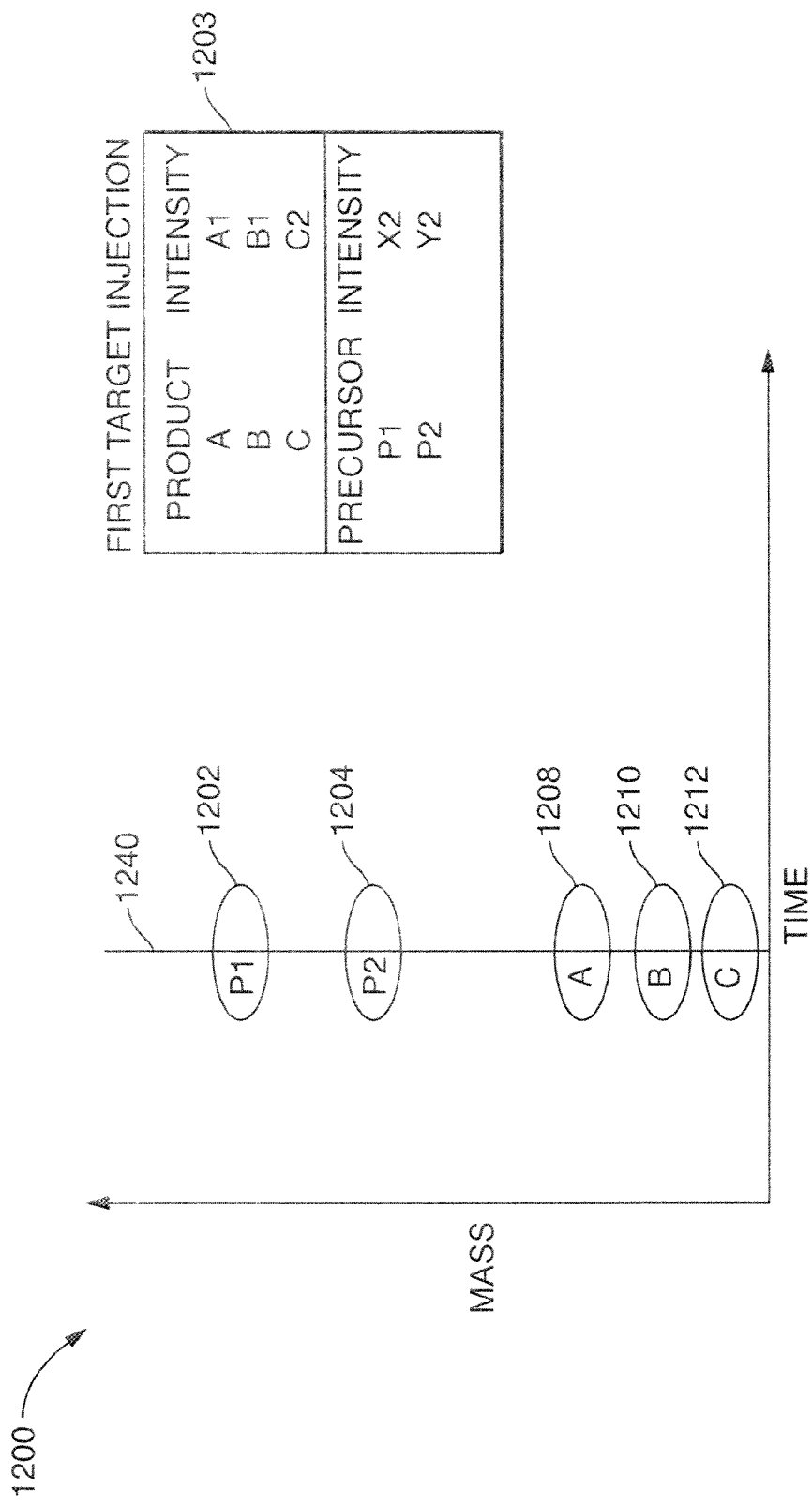

A first target injection is graphically illustrated in FIG. 11A. When performing processing of the first target injection for the precursor 1202, the first target injection may be searched for an ion having the mass of 1202 and having a retention time, with respect to 1240, within the second threshold of the retention time used to track precursors between injections. In this first target injection, a precursor having the mass of 1202 also occurs at a retention time 1240. In this first target injection, product ions 1208, 1210 and 1212 occur at the retention time 1240 within the specified retention time window when determining product ions related to the precursor. Table 1203 illustrates the intensities associated with the products and precursors in the spectrum of 1200.

When performing analysis using the first target injection 1200 with respect to precursor 1204, the first target injection is searched for an ion having the mass of 1204 and having a retention time within the second threshold with respect to the retention time represented by 1260. In this instance, an ion having the mass of 1204 occurs at retention time 1240 but not 1260 and the retention times 1240 and 1260 may not be within the limits of the second threshold. Thus, precursor 1204 of the reference injection having retention time 1260 is not matched or tracked with precursor 1204 of the first injection occurring at retention time 1240. An embodiment using the techniques herein may then treat each of the foregoing occurrences of precursor 1204 as a different precursor since, although both precursors have a mass within a mass tolerance, both precursors in the two injections do not have a common retention time within the second threshold. Accordingly, information may be recorded using the techniques herein for each of the foregoing occurrences of precursor 1204. Table 1203 includes the intensities associated with the product ions and precursor ions of the example 1200. It should be noted that although FIG. 10 is the reference injection, a precursor occurring in a target injection which is not matched or tracked with any precursor in the reference injection may be treated as a new precursor for which additional tracking is performed. In other words, processing may be performed to track this new precursor of FIG. 11A in the other injections of FIGS. 10 and 11B.

Figure 11B:
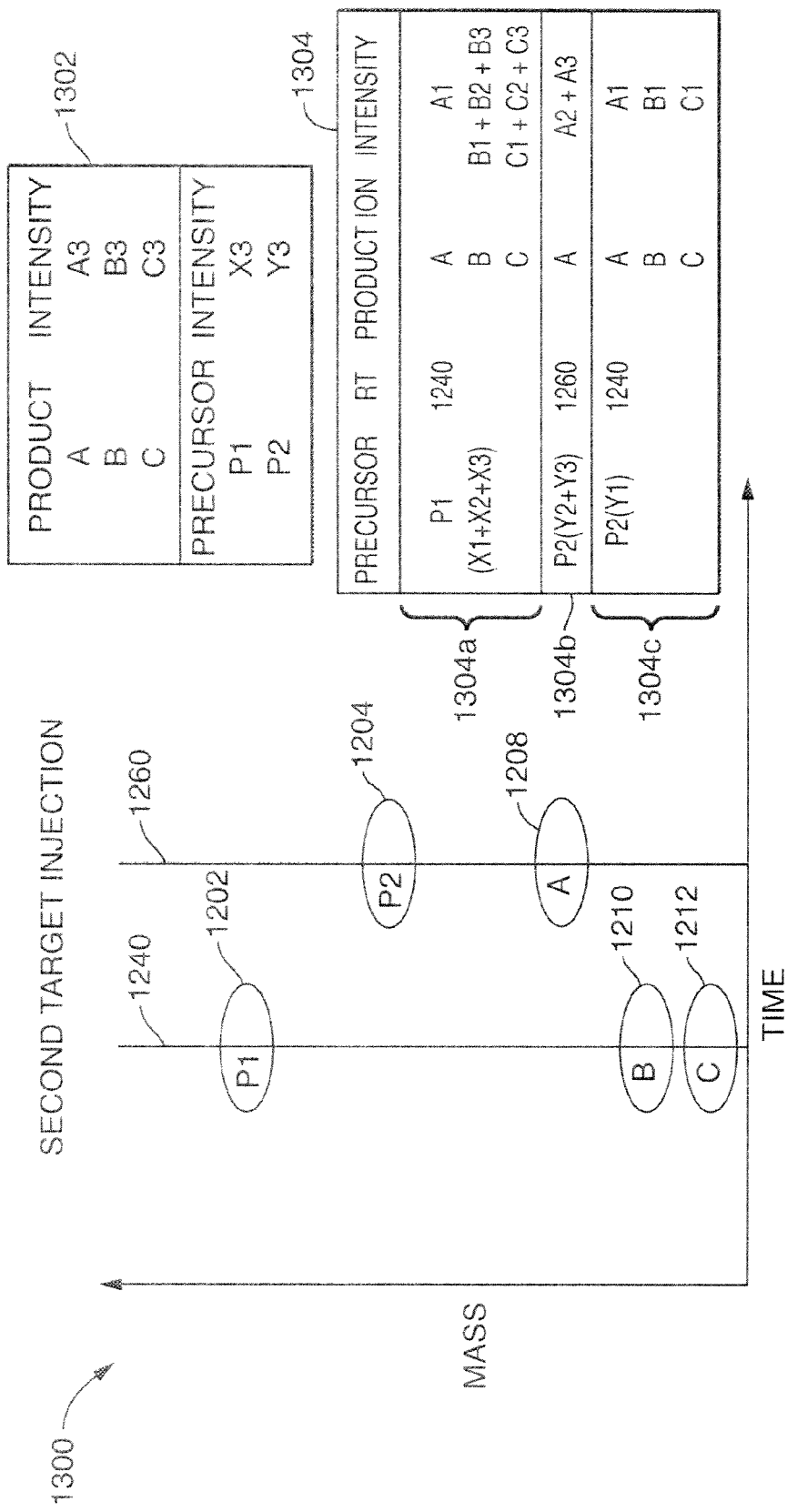

Referring to FIG. 11B, illustrated is a second target injection. The second target injection provides information regarding masses and retention times for the precursor and product ions as previously illustrated and described for the reference injection of FIG. 10. Product and precursor ion intensities are included in table 1302. In accordance with the techniques herein, information may be collected as represented in table

1304. Table 1304 includes the results of applying the set UNION processing techniques described herein to determine a set of product ions and associated intensity sums for each precursor over the injections illustrated in FIGS. 10, 11A and 11B in accordance with the data of tables 1203, 1252, and 1302. It should also be noted that the table 1304 includes intensity sums for each precursor. For precursor P1 1202 having intensity sum "X1+X2+X3", the set UNION operation is applied with respect to the product ions associated with P1 in the reference spectrum and P1 in the first and second target injections resulting in the information of 1304a. For precursor P2 1204 occurring at retention time (RT) 1260 having intensity sum "Y2+Y3", the set UNION operation is similarly applied with respect to the product ions associated with P2 having RT=1260 resulting in the information of 1304b. For precursor P2 1204 occurring at retention time (RT) 1240 having intensity sum "Y1", the set UNION operation is similarly applied with respect to the product ions associated with P2 having RT=1240 resulting in the information of 1304c.

As illustrated by the foregoing, two precursors, as well as product ions, having different retention times may have a same measured retention time in one injection, such as the injection illustrated in FIG. 11A. However, two precursors as well as their respective product ions will have different retention times in repeated experiments. Using the techniques herein, information of table 1304 may be compiled. An embodiment may select a portion of the information of table 1304 for use in connection with subsequent processing such as for protein discovery and identification. In one embodiment, the table 1304 may be examined to determine those precursors having a same mass but different RTs. As an example, entries for 1304b and 1304c are determined. An embodiment may select to use only one of the foregoing entries based on which precursor entry has the largest intensity. It may be that Y2+Y3 represents a larger intensity than Y1 so that the information of 1304b may be used rather than 1304c. An embodiment may similarly only subsequently use collected information of 1304 for a selected number of most intense precursors (e.g., top 2 precursors having the largest intensity of all precursors), only the precursors having an intensity above a threshold intensity, and the like.

Using the Sumtrack technique, a set of product ions which are related to a precursor are determined using a set UNION operation so that the product ion is included in the set if the product ion is determined as related to the precursor in at least one injection (e.g, the product ion is within the retention time window associated with the precursor in at least one injection). By associating an intensity sum produced by summing the intensities for each unique related product ion across multiple injections, those product ions have the largest intensity may be determined and used in connection with identifying the precursor. In other words, the intensity sums associated with product ions for a given precursor may be used in ranking the product ions associated with the precursor. After such ranking, a portion of the product ions may be selected as those having the largest intensity sums. For example, the top ranked "m" product ions representing the m product ions having the largest intensities may be selected for subsequent use. An embodiment may include in the protein profile described herein for a precursor a number of most intense product ions determined using Sumtrack, or others of the techniques herein. The profile may include the mass as well as possibly other information for each such product ion.

As described herein, an embodiment may optionally perform processing of an input sample prior to processing by a mass spectrometer. Such processing may complement or replace separation by liquid chromatographic separation in an embodiment. In one embodiment, the sample may be a mixture of one or more molecules, such as peptides or proteins. Prior to performing mass spectrometry, an embodiment may separate various proteins in the mixture using two-dimensional gel electrophoresis (2DE). The resulting spots may be excised and digested to break the proteins into shorter polypeptide chains. These digests may be analyzed via mass spectrometry. In this particular example, the substance may be a mixture of one or more molecules, for example, such as peptides or proteins. An input sample or substance which includes proteins may be digested as part of enzymatic digestion processing. This enzymatic digestion processing is one type of separation processing that breaks the proteins in the sample into shorter polypeptide chains. Subsequently, the digests may then be further separated using another separation processing technique such as, for example, liquid chromatography (LC), as described above, 2D Gel separation, and the like. It should be noted that generally any separation technique and/or digestion technique may be used to separate the various polypeptides in accordance with, for example, molecular weight, electrical fields and the like. The foregoing separation may optionally be performed in an embodiment on a sample prior to undergoing mass spectrometry and generated spectra or other forms of data that may be included in the input data set for retention time matching.

It should be noted that as used herein, a first measured retention time of a precursor in a first injection may be characterized as substantially the same as a second measure retention time of a product ion in the first injection if the foregoing two measured retention times are within the retention time window such as described above for use in matching precursors with product ions. The precursor and the product ions may be deemed to have the same retention time even though the actual measured retention times may vary.

In connection with tracking precursors between injections, different techniques and criteria may be used in order to determine when a same precursor occurs in different injections. One such technique is described in International Publication No. WO 2005/079261 A2 mentioned above. More generally, one or more criteria may be specified for use in determining whether two precursors in different injections are the same. One embodiment may use criteria including whether the retention times of each are within a second threshold or predetermined window and if the masses of each are within a specified mass tolerance as described elsewhere herein. It should also be noted that the techniques for retention time matching and product ion selection may be applied to samples which are processed using the fractionation techniques described, for example, in PCT International Publication No. WO 2006/133191 A2, PCT Patent Application No. PCT US2006/021919, published on Dec. 14, 2006, METHODS AND APPARATUS FOR PERFORMING RETENTION-TIME MATCHING, Gorenstein et al. which is incorporated by reference herein, in connection with fractionation of a protein mixture.

Figure 12:
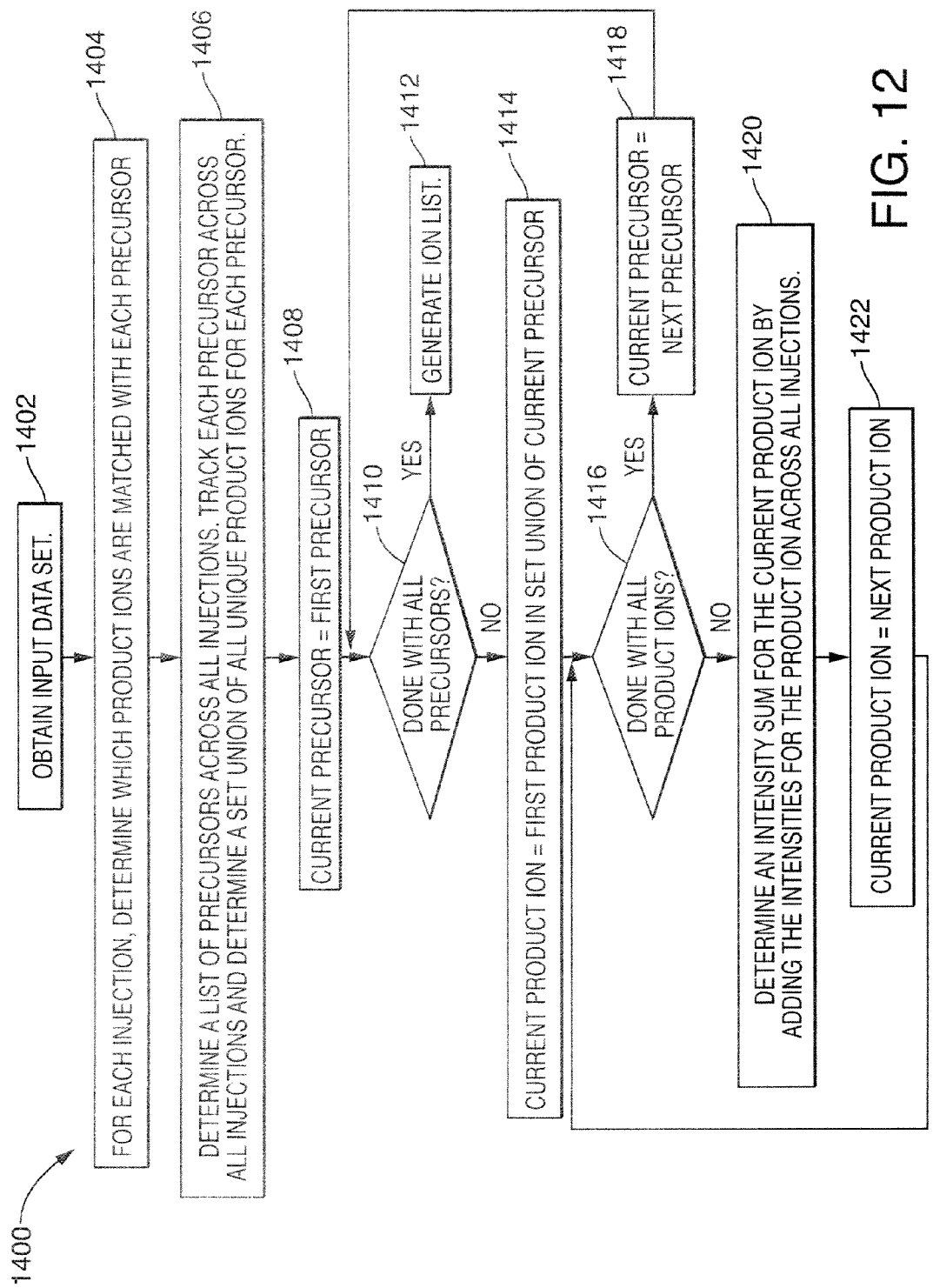
FIG. 12 is a flow diagram of processing steps utilizing the first technique, Sumtrack, described herein in accordance with one embodiment of the invention.

Referring to FIG. 12, show is a flowchart of processing steps that may be used in an embodiment in connection with performing retention time matching and product ion selection of a precursor and its related product ions using Sumtrack. The steps of flowchart 1400 of FIG. 12 present a more general form of processing steps as described in connection with FIGS. 4-5 for injections including multiple precursors and related product ions. At step 1402, the input data set is obtained. The input data set may include multiple injections in which each injection includes multiple precursors. In step 1404, for each of the injections, each precursor is matched with its product ions. As described herein, a precursor may be matched with its product ions by finding those product ions having substantially the same measured retention time and peak shape as the precursor. As also described herein, a determination as to which ions are precursors may be determined using any one or more different techniques. For example, ions produced using the LE mode or cycle as described in Bateman may be determined as precursors. As another example, those one or more ions having a mass or m/z above a certain value with a particular intensity may be determined as precursors. Precursors and product ions having substantially the same retention time in an injection may be determined as those product ions within the retention time window of error with respect to the retention time of the precursor as described elsewhere herein. As a result of step 1404, precursors and related product ions are determined.

At step 1406, a list of precursors is determined with respect to all injections of the input data set. The list of precursors is a list of different or unique precursors as may be generated by determining which precursors appearing in different injections refer to the same precursor. A first precursor in a first injection and a second precursor in a second injection may be determined as a match if the mass of the second precursor is within a defined mass tolerance with respect to the mass of the first precursor, and if the retention time of the second precursor is within the second window or threshold of retention time with respect to the retention time of the first precursor. A technique that may be used in connection with tracking precursors across injections to determine which precursors in different injections refer to the same precursor is also described in International Publication No. WO 2005/079261 A2 mentioned above. As part of step 1406, for each precursor on the list tracked across all injections, a set UNION of all unique related product ions is determined. As described above, two product ions in different injections having masses within a predetermined mass tolerance may be deemed to be the same product ion appearing in two different injections. Step 1406 may include determining which injections include a particular precursor. For each injection including the precursor, a set UNION operation is performed with respect to the product ions of the injection which are related to the precursor (e.g., as determined in connection with step 1404). The set representing the UNION of all such product ions for a particular precursor may be further compressed to determine unique product ions by determining which product ions in different injections have masses within a predetermined mass tolerance. As described elsewhere herein, two product ions in two different injections with masses within the predetermined mass tolerance may be deemed to be the same product ion appearing in the two injections.

As a result of step 1406 processing, a list of unique precursors across all injections is determined. Additionally, for each precursor on the list, a set of related, unique product ions is also determined. For each such product ion, an intensity sum may be determined by adding the intensities for the product ion across all injections. Processing beginning at step 1408 traverses the list of precursors and determines the foregoing intensity sums for the product ions. At step 1408, current precursor is assigned to be the first precursor on the list. At step 1410, a determination is made as to whether all precursors on the list have been processed. If not, control proceeds to step 1414 to traverse the set of product ions for the current precursor. At step 1414, current product ion is assigned the first product ion in the set UNION for the current precursor. At step 1416, a determination is made as to whether all product ions of the current precursor have been processed. If step 1416 evaluates to no, control proceeds to step 1420 to determine an intensity sum for the current unique and related product ion by adding the intensities for the product ion across all injections. As described elsewhere herein, two product ions in two different injections and having mass values within a mass tolerance may be determined to be the same product ion occurring in the two injections. The intensities associated with the foregoing occurrences of the product ion across the different injections may be added to determine the intensity sum for the product ion. It should be noted that the product ion may not be included in each injection so the intensity sum is determined by adding the intensities associated with the injections in which the related product ion and precursor appear. Control proceeds to step 1422 where the current product ion is assigned to be the next product ion in the set for the current precursor. Control proceeds to step 1416. Processing continues with the product ions for the current precursor until complete when step 1416 evaluates to yes. If step 1416 evaluates to yes, control proceeds to step 1418 and then to step 1410 to process the next precursor on the list. Step 1410 evaluates to yes when all precursors on the list have been processed. If step 1410 evaluates to yes, control proceeds to step 1412 to generate an ion list.

In this example, the ion list may include the precursors and related unique products along with the intensity sum for each such product. Information that may be included in an ion list is described elsewhere herein. The ion list of step 1412 may include, for each precursor, all product ions determined along with the associated intensity sum of each product ion. The ion list may also be subsequently ranked. A portion of the ranked product ions may be selected to include, for example, at most a predetermined number, "X", of product ions for each precursor determined in accordance with the intensity sums for the product ions. The product ions for each precursor may be ranked or sorted by intensity sums and those "X" product ions having the maximum intensity sums may be included in the ion list. In one embodiment, a same sample may be used for multiple injections (e.g., replicate injections) processed using the steps of FIG. 12. The resulting ion list may be used in identification of the sample, proteins in the sample, and the like. As another example, each injection may use a different sample mixture.

What will now be described is yet another example of how the Sumtrack technique herein may be used in connection with an input data set obtained using a number of different samples, with a set of replicate injections for each sample. As an example, the input data set may include data related to 60 injections obtained using 20 different samples with 3 replicate injections for each sample. Each of the 20 different samples may correspond to a different condition, diseased state, and the like.

Figure 13:
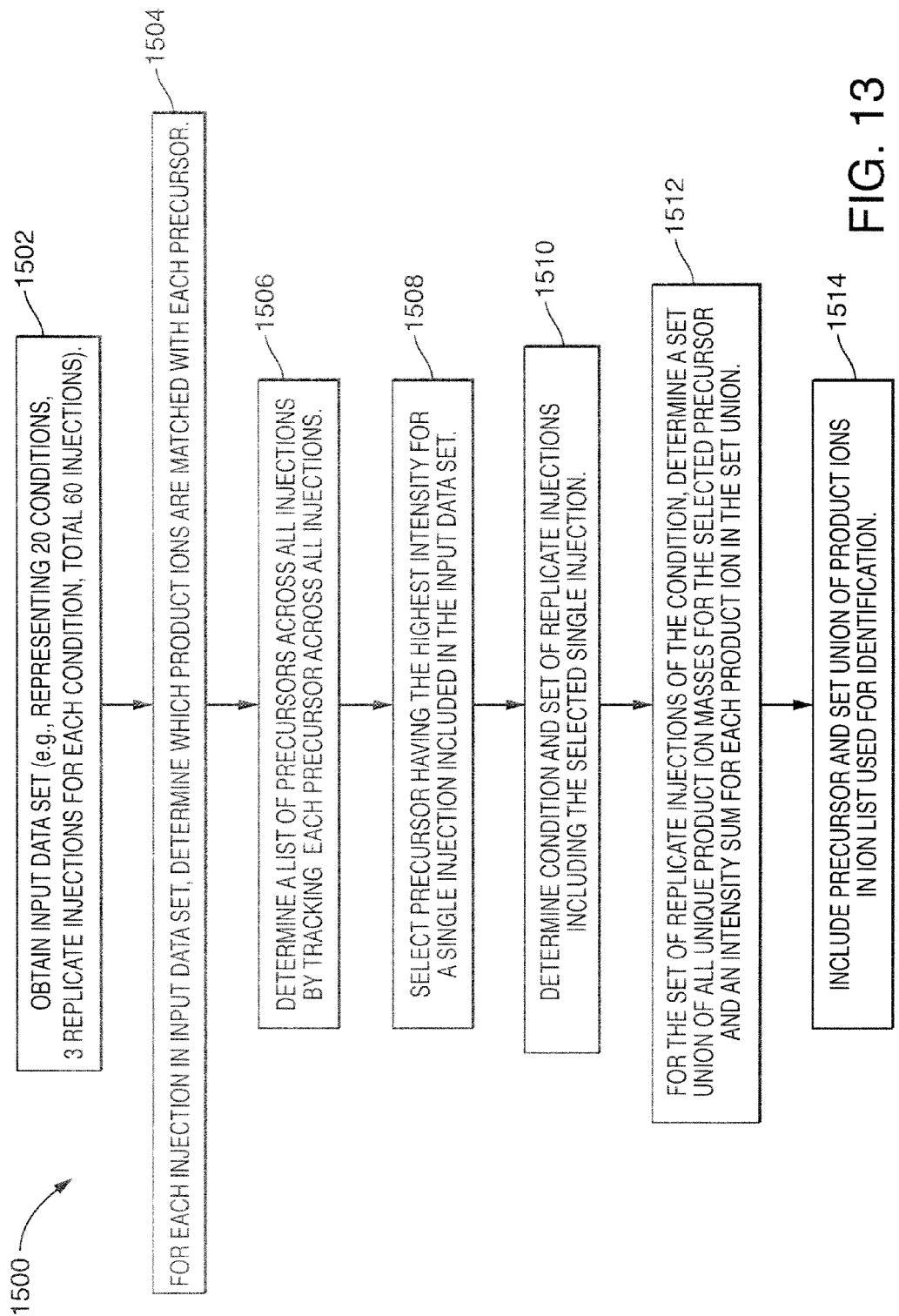
FIG. 13 is a flow diagram of processing steps utilizing the first technique, Sumtrack, described herein in accordance with another embodiment of the invention.
Figure 14:
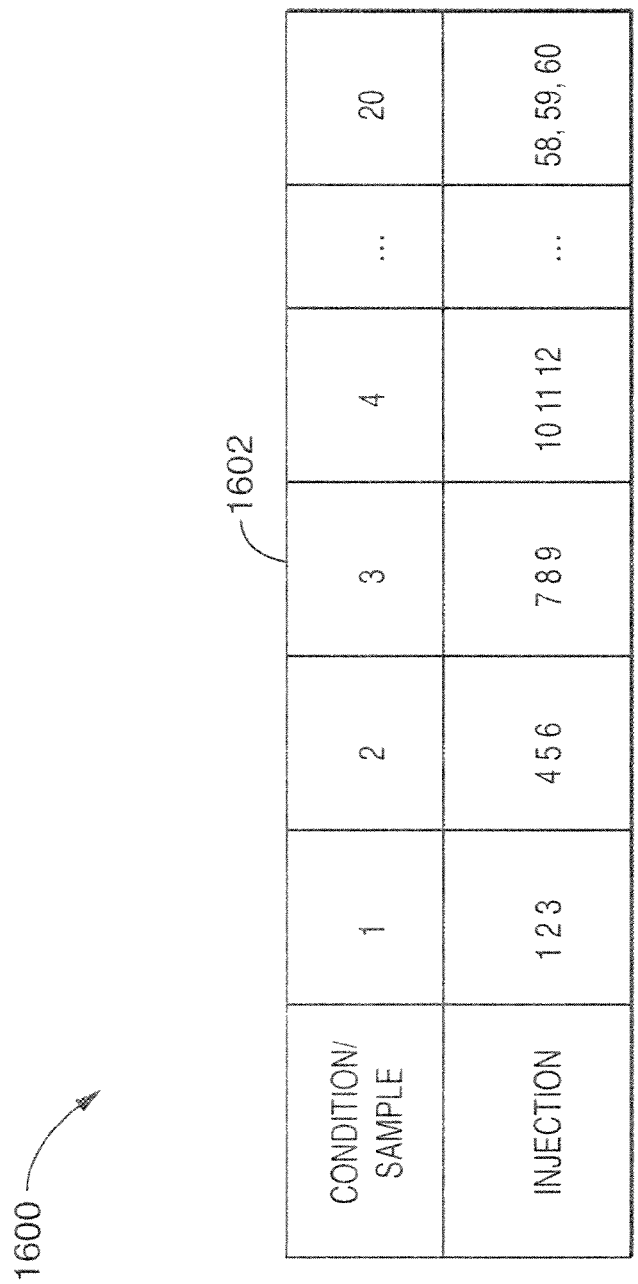
FIG. 14 is an illustration of injections and associated samples that may be used to form an input data set used in connection with the first technique, Sumtrack, described herein in accordance with one embodiment of the invention.

Referring to FIG. 13, shown are processing steps that may be performed in an embodiment using the Sumtrack technique. The steps of the flowchart 1500 may be performed using an input data set obtained as described above. At step 1502, the input data set, such as for the foregoing 60 injections, may be obtained. FIG. 14 is an example 1600 illustrating how each of the 20 samples may be associated a set of 3 replicate injections obtained for each sample. In step 1504, for each injection in the input data set, it is determined which product ions are matched with each precursor. Processing of step 1504 is similar to step 1404 of FIG. 12. At step 1506, a list of unique precursors is determined across all injections by tracking each precursor across all injections. Step 1506 processing is similar to a portion of the processing described above in connection with step 1406 of FIG. 12.

In step 1508, the precursor having the highest intensity for a single injection may be selected from the list. In step 1510, the condition or sample and associated set of replicate injections including the selected single injection from step 1508 is determined. For example, with reference to FIG. 14, it may be determined at step 1508 that a first precursor included in injection 7 has the greatest intensity of all precursors on the list. Subsequently, step 1510 may then determine that the associated condition or sample for injection 7 is 3. The set 1602 of replicate injections 7, 8 and 9 is associated with sample 3.

At step 1512, for the set of replicate injections determined in step 1510, a set UNION of all unique product ion masses for the selected precursor is determined. Additionally, an intensity sum is determined for each unique product ion mass related to the selected precursor. As described elsewhere herein, two product ions occurring in different injections and having mass values within a predetermined mass tolerance may be determined as two occurrences of the same product ion. A first product ion mass may be unique with respect to a second product ion mass if both the first and second product ions masses are not within a predetermined mass tolerance. Step 1512 processing includes performing the set UNION operation for all product ions as described herein for a selected set of injections (e.g., 7, 8 and 9 of 1602) in which the product ions are unique and related to a single precursor (e.g., the precursor determined as having the maximum intensity in the single injection 7). Processing as may be performed in step 1512 in forming the set UNION, determining unique and related product ions for the selected precursor, and determining the intensity sums for such product ions is described elsewhere herein. At step 1514, the precursor and set UNION of the unique and related product ions, along with an intensity sum for each such product ion, may be included in an ion list used for identification or other purposes.

Processing of FIG. 13 may be repeatedly performed for a number of most intense precursors from the input data set. For each precursor, those product ions having the largest intensities may be determined. Information related to the precursors and related product ions determined using FIG. 13 processing may be stored, for example, in a database and used in connection with identifying which proteins occur in the analyzed sample. Additionally, the information may also be used to update, or annotate, information on a matched protein. As an example, consider a protein profile as described herein stored in an existing catalog. Each protein profile used to identify a protein may include information on one or more precursors and related product ions as described elsewhere herein in more detail. A search may be performed to identify a protein from the catalog having a protein profile which matches the one or more precursors and related product ions determined using processing of FIG. 13. In this example, one of the precursors in the protein profile may only have 2 associated product ions. Using the techniques of FIG. 13, a third product ion may be determined for the precursor and added to the existing protein profile. Depending on the information stored in the catalog, criteria used to determine a matching protein, and the like, additional information obtained using processing described herein regarding product ions, precursors, and the like, may be added to the protein profile.

What will now be described is more detail is the Hitrack technique. As mentioned above, Hitrack determines that, for a given precursor, the output data set includes the product ion spectrum associated with the spectrum of the input data set in which the precursor has the greatest intensity. In an embodiment in which the input data set includes 3 spectra, each of which is for a different injection and a same precursor is tracked in all 3 spectra, Hitrack selects the spectrum in which the precursor is the most intense. The product ions in the selected spectra which are retention time matched with the precursor are included in the output data set.

Figure 15:
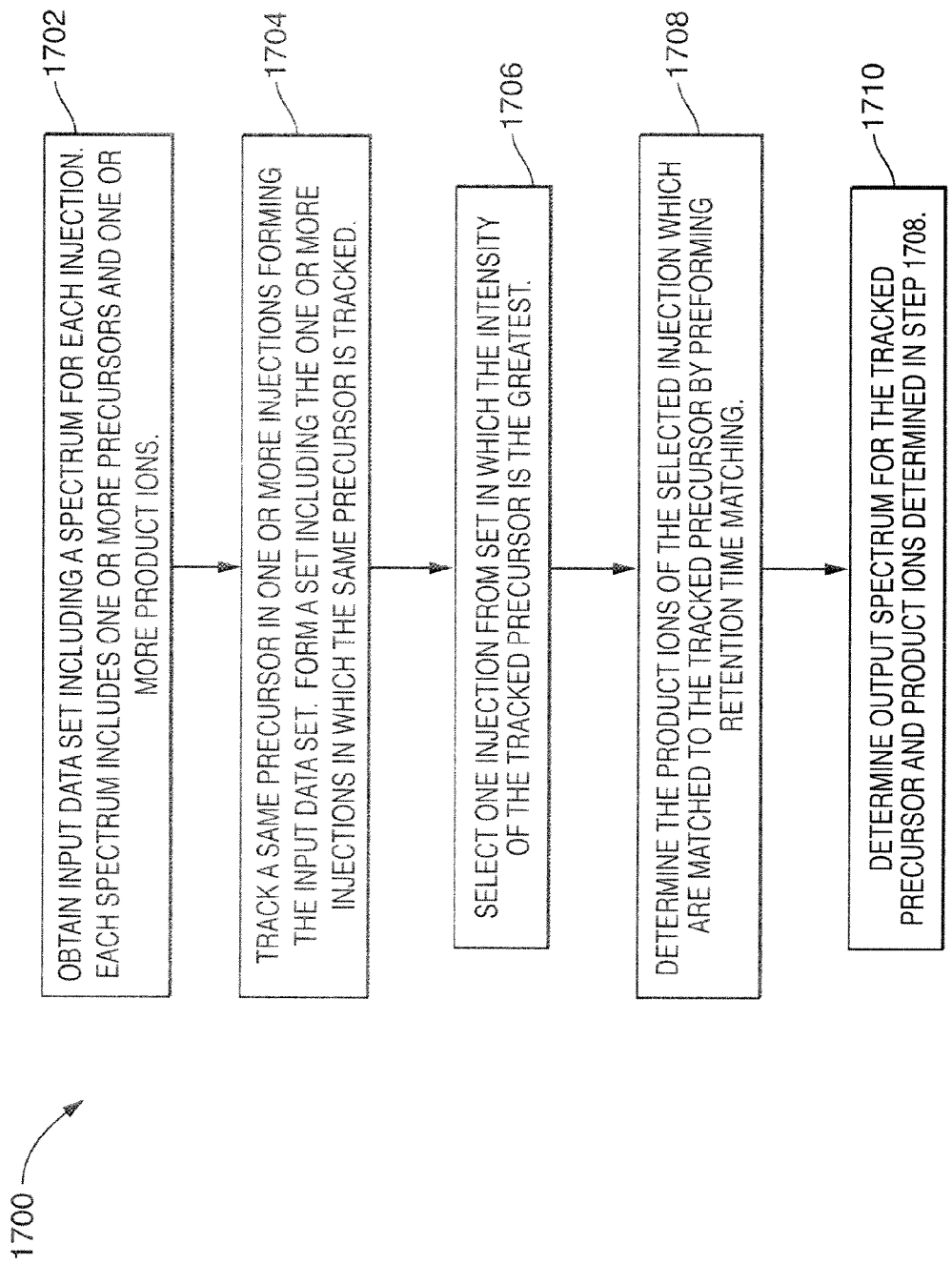
FIG. 15 is a flowchart of processing steps that may be used to determine a precursor and its related product ions using another technique, Hitrack, in accordance with an embodiment of the invention.

Referring to FIG. 15, shown is a flowchart of processing steps that may be performed in an embodiment of the Hitrack technique. At step 1702, an input data set is obtained. In this example, the input data set includes a spectrum for each injection. Each spectrum in the data set includes data for one or more precursors and one or more product ions. In step 1704, a same precursor may be tracked in one or more injections forming the input data set. Tracking a precursor across one or more injections is described elsewhere herein in more detail. A set is formed which includes the one or more injections in which the same precursor is tracked. At step 1706, the injection is selected from the set determined in step 1704 in which the intensity of the tracked precursor is the greatest or maximum of all injections in the set. At step 1708, retention time matching may be performed using the spectrum in the input data set for the selected injection to determine the product ions of the selected injection which are matched or related to the tracked precursor. At step 1710, the output spectrum is determined as including the tracked precursor and matched product ions determined from step 1708. The output spectrum of step 1710 may include the precursor and only those one or more product ions determined as being related to the precursor. The output spectrum of step 1710, as well as the output spectrum produced as a result of embodiments of the other techniques herein, may be used in subsequent processing for quantitative and/or qualitative analysis as described herein as well as more generally in connection with the uses as will be appreciated by those skilled in the art.

It should be noted that steps 1704-1710 may be performed for each tracked precursor in the input data set to determine an output spectrum for the tracked precursor which includes product ions matched or related to the tracked precursor.

What will now be described in more detail are embodiments of the Mergetrack technique. As mentioned above, an embodiment of Mergetrack may utilize processing and product ion selection criteria associated with the Hitrack and/or Sumtrack techniques described herein. Two exemplary embodiments are described herein. In connection with a first embodiment, for a tracked precursor in one or more spectra, the precursor's intensity in the output spectrum may be determined as the sum of intensities of the precursor across all tracked spectra. Retention time matching of the tracked spectra including the tracked precursor may be performed to determine, for each tracked spectra, which product ions are related to the tracked precursor. Processing and product ion selection criteria of the Hitrack technique may first be applied to the set of spectra including the tracked precursor to determine a first resulting spectrum which is subjected to further processing in subsequent steps. For each product ion included in the first resulting spectrum, processing is performed to identify all instances of the product ion in the set of spectra including the tracked precursor. The foregoing identification of the same product ion in different spectra may be performed as described elsewhere herein by determining matches in accordance with product ion masses. The intensity of the product ion in each of the one or more spectra including the product ion is obtained. The intensity of the product ion in the first resulting spectrum is determined as the sum of the foregoing intensities for the product ion across the one or more spectra where the product ion has the same retention time as the respective tracked precursor. The output spectrum is determined as the first resulting spectrum where the product ions have intensities determined in accordance with the foregoing processing.

Figure 16:
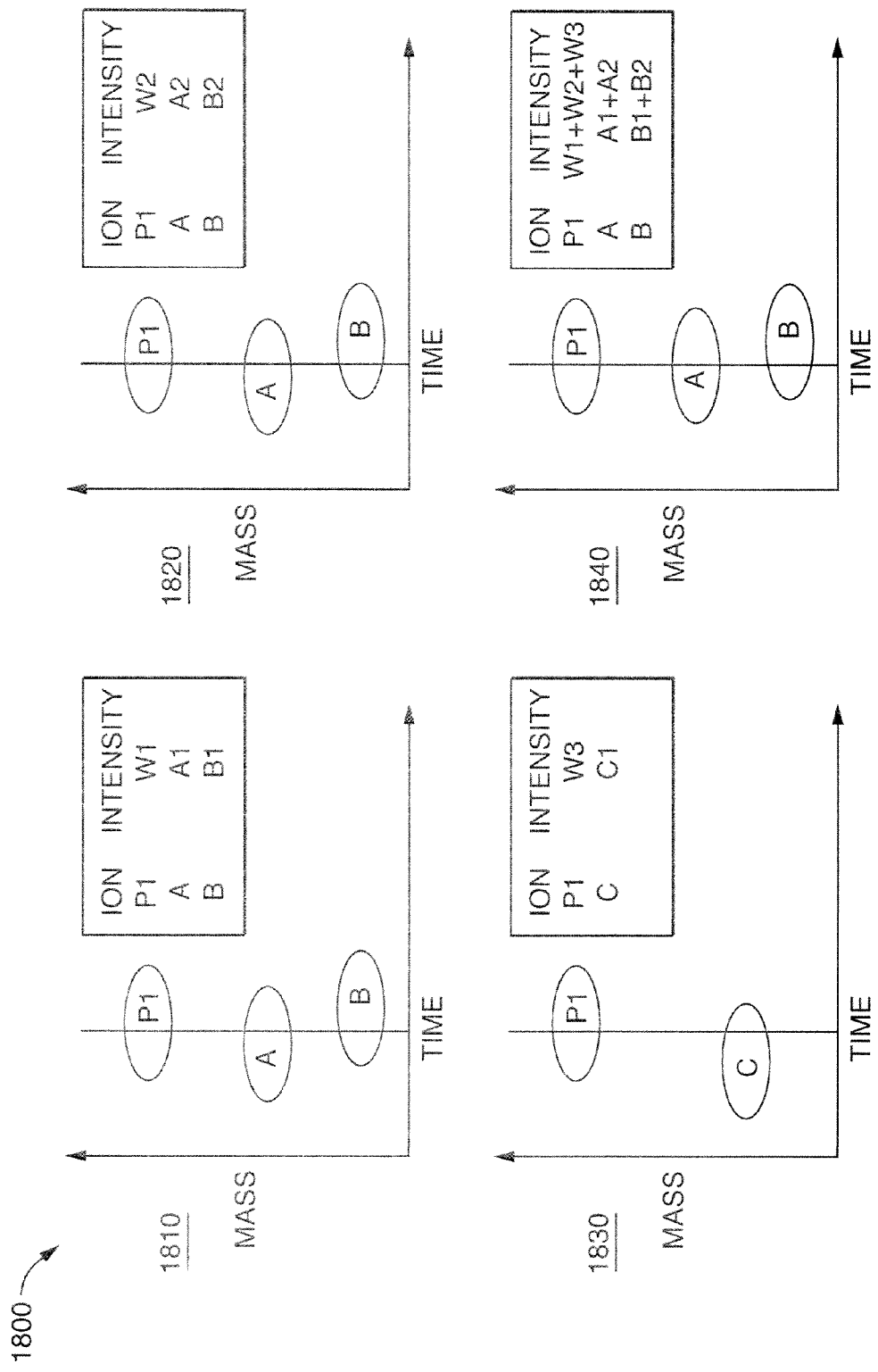
FIGS. 16-17 illustrate an example applying yet another technique, Mergetrack in accordance with embodiments of the invention.

Referring to FIG. 16, shown is an example illustrating one embodiment of Mergetrack processing. The example 1800 includes 4 spectra: 1810, 1820 and 1830 which are 3 spectra in the input data set and 1840 which is the output spectrum. P1 is the precursor tracked across spectra 1810, 1820 and 1830. A, B and C are product ions in connection with 1800. Retention time matching may be performed for each of the 3 spectra including the tracked precursor P1 to determine, for each spectra, product ions which match the tracked precursor. The spectra 1810, 1820 and 1830 may be the results of applying retention time matching as described herein so that each of the spectra includes a precursor and product ions within a retention time window. The intensity of the precursor P1 in the output spectrum 1840 is determined as the sum of intensities of the precursor across all tracked spectra including the precursor. In this example, the intensity of precursor P1 in the output spectrum 1840 is W1+W2+W3. An embodiment of the Hitrack technique may be applied to the 3 spectra including the tracked precursor and, for purposes of illustration, let W1 be the largest of all P1 intensities so that 1810 is selected in accordance with HiTrack processing (e.g., selected in accordance with the criteria used in connection with FIG. 15). As a result, the output spectrum includes the product ions, A and B, matched to the tracked precursor P1 via retention time matching with respect to the selected spectrum 1810. Processing is performed to find other ions in the 3 tracked spectra which match A and B in terms of mass. With respect to the example 1800 in accordance with mass matching techniques described herein, A is determined as also being in 1820 and B is determined as also being in 1820. The intensity for A is determined as the sum of A's intensities across all matching tracked spectra so the intensity of A in 1820, A2, is added to the intensity of A in 1810, A1 so that A's intensity in the output spectrum 1840 is A1+A2. Similarly, the intensity for B is determined as the sum of B's intensities across all matching tracked spectra so the intensity of B in 1820, B2, is added to the intensity of B in 1810, B1 so that B's intensity in the output spectrum 1840 is B1+B2. Note that C is not included in the output spectrum.

Figure 17:
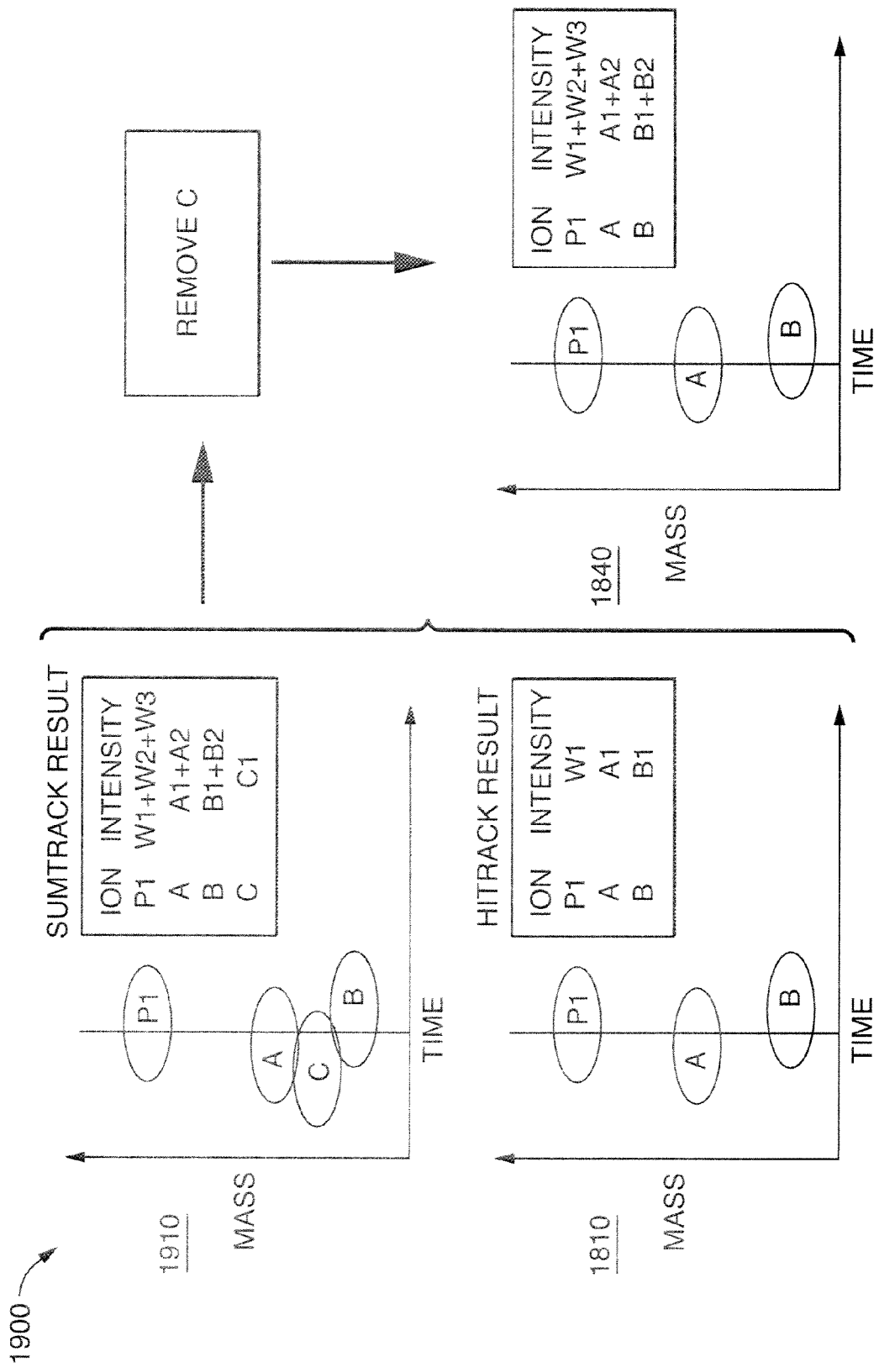

Alternatively, Mergetrack may be implemented in an embodiment using different processing steps than just described to obtain the same output spectrum 1840. An example illustrating this alternative will now be described with reference to FIG. 17. In this alternative embodiment, with respect to the precursor P1 and the tracked spectra 1810, 1820 and 1830 included in the input data set, an embodiment of the Sumtrack technique may perform processing in a first step to determine a first resulting spectrum. Element 1910 represents the foregoing first resulting spectrum for this example and includes the precursor and all product ions which are retention time matched to the precursor in at least one spectrum of the input data set. Element 1910 may be produced, for example, by performing processing steps described herein in connection with FIGS. 4 and 5. In a second step, an embodiment of the Hitrack technique may perform processing using the 3 tracked spectra 1810, 1820 and 1830. Element 1810 is selected as illustrated in FIG. 17. The alternative embodiment then removes from the first resulting spectrum 1910 the product ions which are not included in the spectrum 1810 generated using an embodiment of the Hitrack technique. In this example, C is removed from 1910 resulting in the spectrum 1840.

In the foregoing two embodiments of Mergetrack processing, the product ions selected are those included in the tracked spectrum where the intensity of the tracked precursor is the greatest (with respect to all tracked spectra), and which have a retention time that matches the tracked precursor's retention time. The intensity for each of the precursor and product ions may be an intensity sum corresponding to that as determined in an embodiment of the Sumtrack technique. Both embodiments of the Mergetrack technique herein result in selecting the same set of product ions for a given tracked precursor and determining the same intensities for the product and precursor ions.

Processing of the foregoing two alternative embodiments of the Mergetrack technique will now be summarized. It should be noted that prior to performing processing as will be described in FIGS. 18 and 19 for Mergetrack, retention time matching of the tracked spectra including the tracked precursor may be performed to determine, for each tracked spectra, which product ions are related to the tracked precursor. The spectra used in processing of FIGS. 18 and 19 may be the result of applying retention time matching as described herein so that each of the spectra includes a same precursor and product ions having retention times occurring within a retention time window so that the precursor and product ions are determined as having matching retention times.

Figure 18:
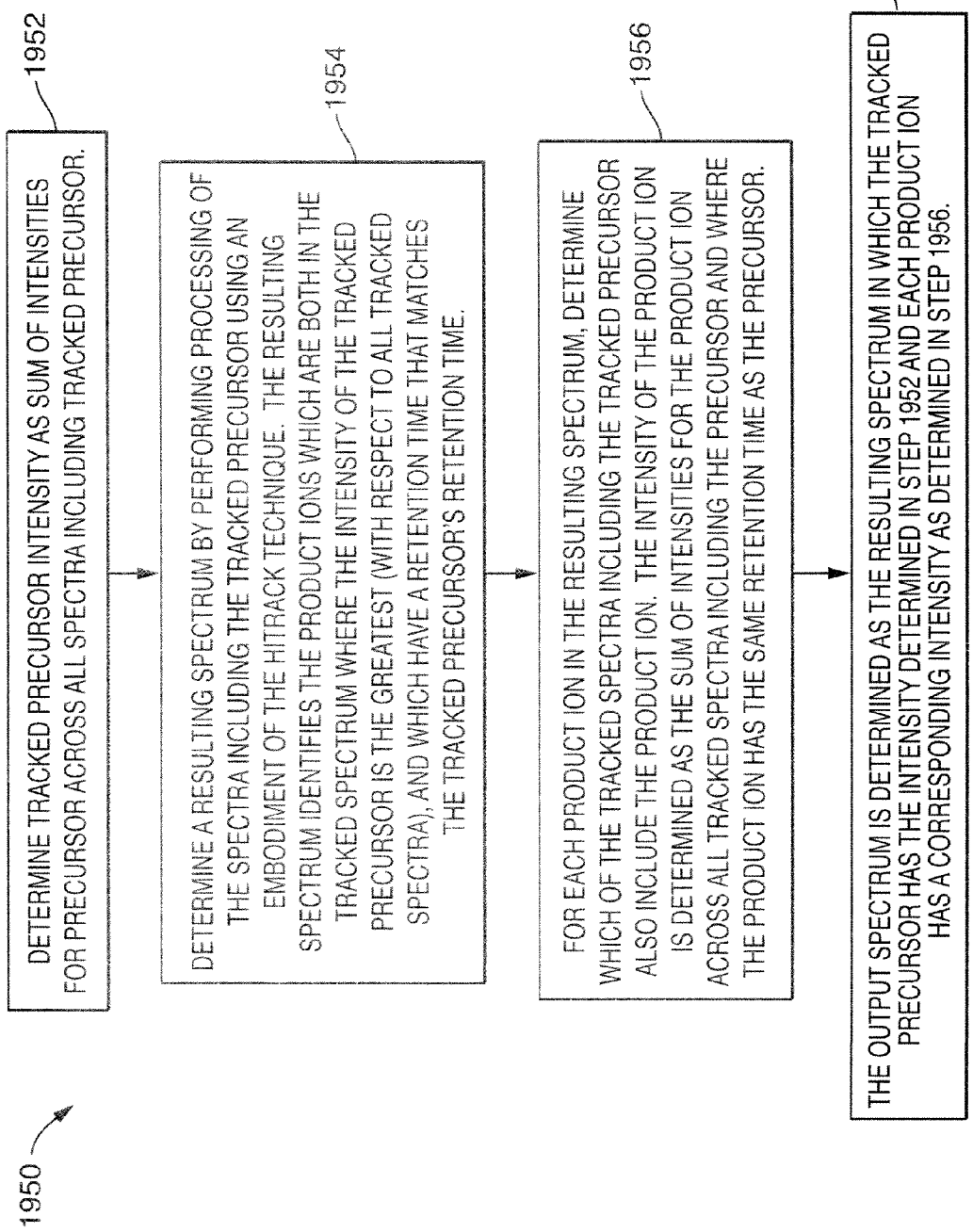
FIG. 18-19 are flowcharts of processing steps of that may be performed in different embodiments of Mergetrack in accordance with the invention.

Referring to FIG. 18, shown is a flowchart of processing steps that may be performed in an embodiment of the Mergetrack technique. The flowchart 1950 summarizes processing for the first approach for performing Mergetrack as described above with reference to FIG. 16. In step 1952, the tracked precursor intensity in the output spectrum is determined as the sum of intensities for the precursor across all tracked spectra. In step 1954, a resulting spectrum is determined by perform processing the tracked spectra including the tracked precursor using an embodiment of the Hitrack technique. Step 1954 may include performing processing as described herein in connection with FIG. 15. The resulting spectrum produced in step 1954 identifies the product ions which are both in the tracked spectrum where the intensity of the tracked precursor is the greatest (with respect to all tracked spectra), and which have a retention time that matches the tracked precursor's retention time. In step 1956, for each product ion in the resulting spectrum of step 1954, it is determined which of the tracked spectra include the product ion. The intensity of the product ion in the output spectrum is determined as the sum of intensities for the product ion across all tracked spectra including the precursor and where the product ion and precursor having matching retention times. In step 1958, the output spectrum is determined as the resulting spectrum, from step 1954, in which the tracked precursor has the intensity determined in step 1952 and each product ion has a corresponding intensity as determined by step 1956.

Figure 19:
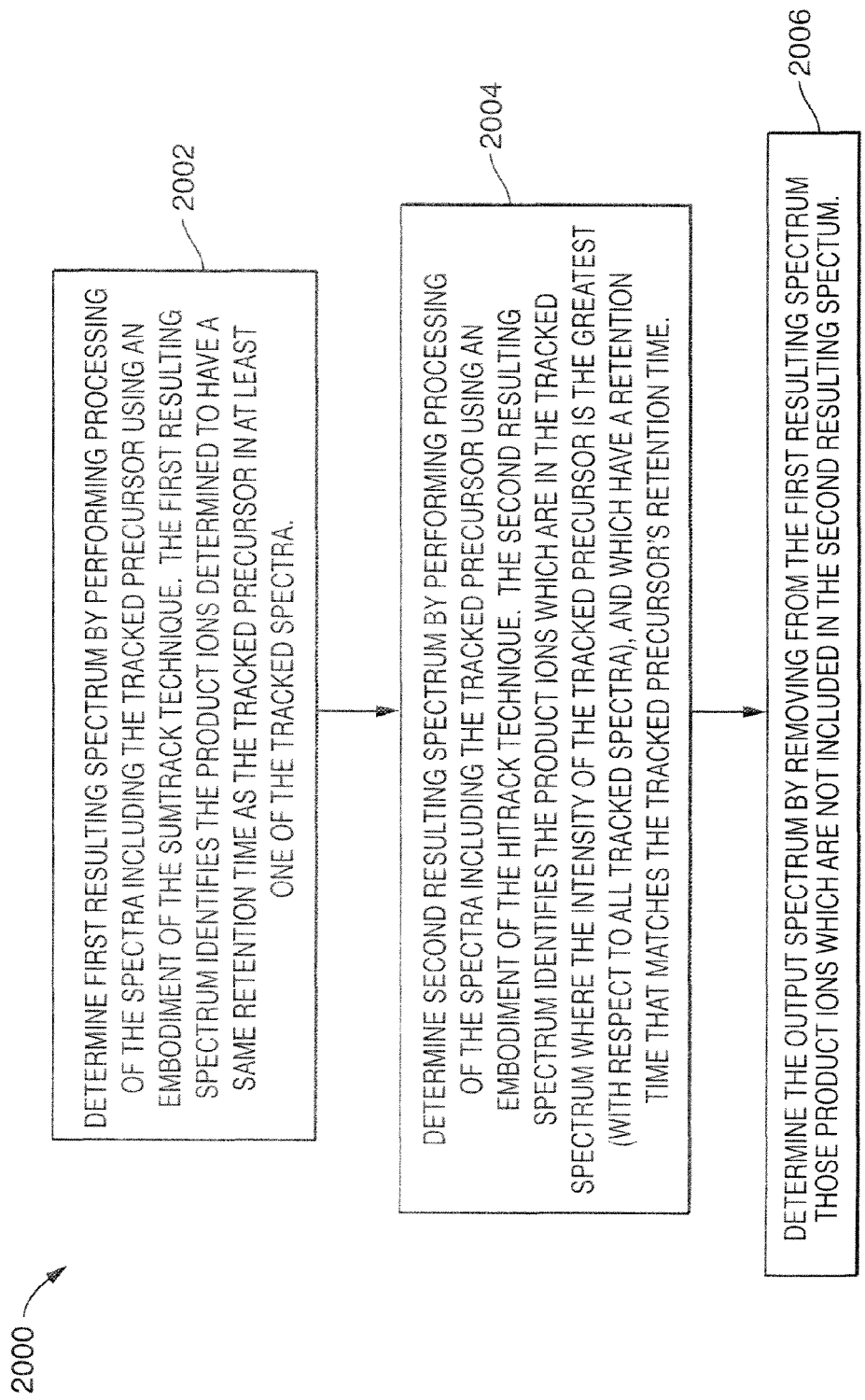

Referring to FIG. 19, shown is a flowchart of processing steps that may be performed in connection with a second embodiment of the Mergetrack technique. The flowchart 2000 summarizes processing for the second approach for performing Mergetrack as described above with reference to FIG. 17. In step 2002, a first resulting spectrum is determined by performing processing of the spectra including the tracked precursor using an embodiment of the Sumtrack technique. The first resulting spectrum may identifies the product ions determined to have a retention time that matches the tracked precursor's retention time in at least one of the tracked spectra. Step 2002 may include performing processing described herein in connection with FIGS. 4 and 5. In step 2004, a second resulting spectrum is determined by performing processing of the spectra including the tracked precursor using an embodiment of the Hitrack technique. Step 2004 may include performing processing as described herein in connection with FIG. 15. The second resulting spectrum identifies the product ions which are both in the tracked spectrum where the intensity of the tracked precursor is the greatest (with respect to all tracked spectra), and which have a retention time that matches the tracked precursor's retention time. In step 2006, the output spectrum is determined by removing from the first resulting spectrum those ions which are not included in the second resulting spectrum determined in step 2004.

The output spectrum produced as a result of processing of FIG. 18 may be the same as the output spectrum produced as a result of processing of FIG. 19.

The processing steps performed in an embodiment utilizing the techniques herein, such as illustrated in FIGS. 4, 5, 12, 13, 18 and 19, may be performed as a result of code executed by a computer processor. The code may be stored on any one of a variety of different forms of computer readable media, memory and the like.

In connection with the techniques described herein in one embodiment, a molecule in a mixture may be separated in a liquid chromatograph and elute in an unmodified form. The foregoing molecule can give rise to one or more ions in an LC/MS system and may also be referred to as the originating molecule. When subjected to the electrospray or other ionization processing, as well as other optional processing as may be included in an embodiment, a resulting mass spectrum of the originating molecule may include more than one ion. Multiple ions can result from, for example, the isotopic distribution of the molecule, the different charge states produced by ionization, and/or fragmentation mechanism applied to the ions, or other modifications imposed subsequent to elution from the LC. Thus, an originating molecule may produce one or more ions. In connection with the techniques described herein, the peak shapes and retention times of ions that derive from the same originating molecule are identical having measurements including retention times which are deemed to be the same.

An ion list as described in connection with the techniques herein may include one or more rows of data. In one embodiment, each row in an ion list contains a retention time, mass/charge, intensity describing an ion. The data about each ion in the ion list may be obtained using any one of a variety of different techniques. For example, the data about one or more of the ions may be obtained using the Bateman technique in the LE or HE mode. An ion list may also refer to a list of AMRTs (Accurate Mass Retention Times), where each row contains a retention time, mwHPlus, intensity, and charge state as may be obtained using LE or HE acquisition mode. AMRTs are described in more detail in "Quantitative Proteomic Analysis by Accurate Mass Retention Time Pairs" by Silva, et al., Anal. Chem., Vol. 77, pages 2187-2200 (2005).

A spectrum included in an input data set used in connection with the techniques described herein may contain a list of ions (or AMRTs), each described by an m/z (or mwHPlus) and an intensity. An embodiment may obtain a spectrum in the input data set using a first technique including data obtained in a single scan as collected by the mass spectrometer. In this case, the ion list for the spectrum corresponds to mass spectral peaks as may be viewed in the spectrum, and the retention time of the spectrum is the acquisition time of the spectral scan. Alternatively, a spectrum may be obtained by selecting a retention time and a retention time window, and collecting all ions from an ion list whose retention time falls within that window as described, for example, in PCT International Publication No. WO 2005/079263 A2, PCT Patent Application No. PCT US2005/004180, published on Sep. 1, 2005, APPARATUS AND METHOD FOR IDENTIFYING PEAKS IN LIQUID CHROMATOGRAPHY/MASS SPECTROMETRY DATA AND FOR FORMING SPECTRA AND CHROMATOGRAMS, Gorenstein et al which is incorporated by reference herein. The retention time of the spectrum may be determined to be, for example, the retention time that lies in the middle of the window represented as $+/-\frac{1}{10}$ of a chromatographic peak width measured at FWHM.

It should be noted that spectrum included in the input data set used in connection with the techniques described herein may be filtered, for example, such as by removing ions (or AMRTS) whose masses or intensities fall outside of a particular range.

In connection with the retention matching and product ion selection techniques herein, the output spectrum may be generated in a form in accordance with one or more output rules. For example, as described herein, a product ion in a first spectrum may have a first measured mass and the same product ion in a second spectrum of the input data set may have a second measured mass. The first and second measured masses may be deemed to be the same mass if they are within a defined mass tolerance. In the output spectrum, the mass for the product ion may be output in accordance with a rule such as, for example, the mass output in the output spectrum may be the average of the first and second measured masses. The output spectrum may, for example, consist solely of masses obtained from either the first or the second spectrum. Other embodiments may use other techniques to determine the values included in the output spectrum. Also, use of the foregoing technique to determine if two masses in two spectra are within a mass tolerance, and if so, determining that the two masses correspond to a same ion in different spectra, may be utilized in connection with the techniques herein. For example, the foregoing may be used to determine whether two product ions in two different spectra are deemed a match, and thus represent the same product ion.

The one or more spectra included in an input data set used with the retention matching techniques may come from a variety of different sources. As described above, a spectrum may be generated in a variety of different ways from one or more experiments. A spectrum or other form of data included in the input data set may also come from a database or other data store. For example, data from previous experiments may be stored in a data base. The previous experimental data from the database, alone or in combination with additional new data, may be included in an input data set. The data included in the database or other data store may include theoretical or simulated experimental data for use in connection with the techniques described herein. A spectrum, for example, acquired using DDA of MS/MS spectra may be included.

In an embodiment in which the sample used to obtain an input data set is a complex mixture of proteins, ions from different proteins may overlap in retention time. For such data, the techniques herein may be applied by selecting a most intense ion in a single injection, and forming a spectrum of all product ions within a retention time window of that most intense ion. This most intense ion may be deemed a precursor ion which is then found in a subsequent injection of substantially the same mixture of proteins by matching masses and retention times for the precursor in both injections as described herein (e.g., masses of each injection within the specified mass tolerance, and retention times of each injection being within the second threshold or window as described above).

In connection with the techniques described herein, isotopic variations and/or variations in charge state may occur for precursor and product ions. Although not expressly included in the processing steps of flowcharts described herein, it will be appreciated by those skilled in the art that the foregoing variations for a particular ion may be recognized and processing may be performed to reduce or summarize such information to process the ion and any such variations as a single entity in accordance with the techniques herein. For example, the foregoing single entity may have a monoisotopic mass for the ion occurring at a specific retention time having a charge state of 1.

Described herein are embodiments of the different retention time matching and precursor selection techniques. It will be appreciated by those skilled in the art that the particular order in which processing steps may be performed in an embodiment may be varied from that described herein.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A method of matching a precursor ion with one or more related product ions comprising:
providing, using a processor, a plurality of input data sets obtained from a plurality of injections, each of said plurality of input data sets including a same precursor ion and one or more product ions;
normalizing, using a processor, said plurality of input data sets in accordance with a single retention time for said precursor ion;
for each of said plurality of input data sets, determining, using a processor, which product ions are within a predetermined retention time window with respect to said single retention time for said precursor ion; and
performing, using a processor, a set union operation with respect to product ions included in said plurality of input data sets whereby if a product ion is within the predetermined retention time window in any of said plurality of input data sets, said product ion is related to said precursor ion having said single retention time.

2. The method of claim 1, further comprising:
determining an intensity sum for each product ion related to said precursor ion having said single retention time, wherein said intensity sum is determined by adding one or more intensities of said each product ion, each of said one or more intensities corresponding to an intensity of said each product ion in a different one of said injections.

3. The method of claim 2, further comprising:
selecting a number of product ions related to said precursor ion in accordance with an intensity sum associated with each of said product ions.

4. The method of claim 3, further comprising:
ranking product ions related to said precursor ion in accordance with an intensity sum associated with each of the product ions.

5. The method of claim 1, wherein said plurality of input data sets are obtained using a sample that includes any of a protein mixture, a serum, a tissue sample, a single polypeptide, and a plurality of proteins.

6. The method of claim 1, wherein a portion of said plurality of input data sets are produced by mass analyzing said precursor ion by alternating between a first low fragmentation mode and a second high fragmentation mode and obtaining a first spectrum for said first low fragmentation mode and a second spectrum for said second high fragmentation mode.

7. The method of claim 1, wherein at least a portion of said plurality of input data sets are spectra.

8. The method of claim 1, wherein at least a portion of said plurality of data sets are ion lists, each ion in said ion lists being annotated with information including a retention time, an intensity, and a mass or a mass to charge ratio for said each ion.

9. The method of claim 1, wherein said plurality of input data sets are obtained using at least one sample including a first protein, and the method further comprising:
providing a catalog of protein profiles, each of said protein profiles defined by an identity of a protein, said catalog including a profile for said first protein; and
updating said catalog by adding information about said first protein, said information including data about said precursor ion and said one or more related product ions.

10. The method of claim 9, further comprising:
identifying one or more unknown proteins of an unknown sample using said catalog, and wherein said identifying includes:
obtaining first data about said unknown sample; and
matching a portion of said first data with said data about said precursor ion and said one or more related product ions included in said catalog to identify said first protein as being included in said unknown sample.

11. The method of claim 1, wherein a first product ion in a first input data set having a first mass and a second product ion in a second input data set having a second mass are determined to be a same product ion if said first mass is within a predetermined mass tolerance window of said second mass.

12. An apparatus for analyzing a sample comprising:
a chromatography module;
a mass-spectrometry module in communication with said chromatography module; and
a control unit in communication with said chromatography module and said mass spectrometry module, said control unit including at least one processor and a memory for storing a plurality of instructions executed by said processor, said plurality of instructions causing said processor to perform:
tracking precursors across a plurality of injections to determine which of said plurality of injections include each of said precursors in accordance with criteria including a retention time and a mass associated with said each precursor;
determining, for each of said precursors, a set of related product ions, wherein said determining a set of related product ions for each precursor includes performing a set union operation with respect to product ions included in said plurality of injections, each of said related product ions having a retention time within a predetermined retention time window with respect to said retention time of said each precursor in any of said plurality of injections; and
determining, for each of said related product ions of each of said precursors, an intensity sum, wherein said intensity sum is determined by adding one or more intensities of said each related product ion, each of said one or more intensities corresponding to an intensity of said each related product ion in a different one of said plurality of injections including said each precursor.

13. The apparatus of claim 12, wherein said tracking of a precursor includes:
determining a first retention time for a first precursor in a first injection and a second retention time for a second precursor in a second injection,
determining whether said first retention time and said second retention time are within a retention time tolerance;
determining a first mass for said first precursor and a second mass for said second precursor;
determining whether said first mass and said second mass are within a mass tolerance; and
if said first retention time and said second retention time are within said retention time tolerance, and said first mass and said second mass are within said mass tolerance, determining that said first precursor and said second precursor are instances of a same precursor occurring in different injections.

14. A method of matching a precursor ion with one or more related product ions comprising:
   providing, using a processor, a plurality of input data sets, wherein each of said plurality of input data sets is obtained from a different one of a plurality of injections, each of said plurality of input data sets including a same precursor ion having a first retention time and one or more product ions having a retention time within a predetermined retention time window with respect to said first retention time for said precursor ion;
   selecting, using a processor, a first of the input data sets in which an intensity of said precursor ion is a maximum with respect to an intensity of said precursor in others of said plurality of input data sets;
   after said selecting selects the first input data set in which the intensity of the precursor ion is the maximum, determining, using a processor, a first set of product ions using the first input data set selected in said selecting, wherein each product ion in the first set is in said first input data set selected by said selecting and has a retention time within said predetermined retention time window with respect to said first retention time; and
   for each product ion in said first set, determining, using a processor, as a first result which of said plurality of input data sets include said each product ion having a retention time that is within said predetermined retention time window with respect to said first retention time, and determining an intensity sum for said each product ion by summing intensities of said each product ion across input data sets in said first result whereby each of said intensities of said each product ion that is summed is an intensity of said each product ion in a different one of the plurality of input data sets included in the first result, wherein said first set of product ions are related to said precursor and each of said product ions in said first set has an intensity sum as determined by said step of determining an intensity sum.

15. The method of claim 14, further comprising:
   determining an output data set including said precursor having an intensity which is a sum of intensities for said precursor across said plurality of input data sets, said output data set including each product ion in said first set and said each product ion having an intensity sum as determined in said first determining step, said output data set including product ions related to said precursor.

16. The method of claim 14, wherein said predetermined retention time window is determined using a width and a threshold, wherein said width is a chromatographic peak width determined as a full width half maximum peak of a mass spectral peak of the precursor ion, said threshold is $1/10^{th}$ of said width, said predetermined retention time window has a lower bound determined by subtracting said threshold from said width, and said predetermined retention time window has an upper bound determined by adding said threshold to said width.

17. The method of claim 14, wherein a portion of said plurality of input data sets is produced by mass analyzing said precursor ion by alternating between a first low fragmentation mode and a second high fragmentation mode and obtaining a first spectrum for said first low fragmentation mode and a second spectrum for said second high fragmentation mode.

18. The method of claim 17, wherein said plurality of input data sets are obtained using a sample that is a digested protein, and the method further comprising:
   performing LC/MS on said digested protein.

19. A method of matching a precursor on with one or more related product ions comprising:
   providing, using a processor, a plurality of input data sets obtained from a plurality of injections, each of said plurality of input data sets including a same precursor ion having a first retention time and one or more product ions having a retention time within a predetermined retention time window with respect to said first retention time for said precursor ion;
   determining, using a processor, a first set of product ions, wherein said determining a first set of product ions includes performing a set union operation with respect to product ions included in said plurality of input data sets whereby each product ion in said first set has a retention time within said predetermined retention time window with respect to said first retention time in any of said plurality of input data sets, each product ion in said first set having an intensity that is a sum of intensities of said product ion across input data sets in said plurality which include said each product ion, and in which said each product ion has a retention time within said predetermined retention time window with respect to said first retention time;
   selecting, using a processor, a first of the input data sets in which an intensity of said precursor ion is a maximum with respect to an intensity of said precursor in others of said plurality of input data sets;
   determining, using a processor, a second set of product ions wherein each product ion in said second set is included in said first input data set selected by said selecting and has a retention time within said predetermined retention time window with respect to said first retention time; and
   removing, using a processor, product ions from said first set which are not included in said second set, wherein, after performing said removing, said first set includes product ions related to said precursor.

20. The method of claim 19, further comprising:
   determining an output data set including said first set of product ions after performing said removing, said output data set including said precursor having an intensity that is a sum of intensities of said precursor across said plurality of input data sets, each product ion in said first set having an intensity as determined by said step of determining a first set of product ions.

21. The method of claim 19, wherein a portion of said plurality of input data sets is produced by mass analyzing said precursor ion by alternating between a first low fragmentation mode and a second high fragmentation mode and obtaining a first spectrum for said first low fragmentation mode and a second spectrum for said second high fragmentation mode.

22. The method of claim 21, wherein said plurality of input data sets are obtained using a sample that is a digested protein, and the method further comprising:
   performing LC/MS on said digested protein.

23. A non-transitory computer readable medium comprising executable code stored thereon for matching a precursor ion with one or more related product ions, the non-transitory computer readable medium comprising executable code for:
   providing a plurality of input data sets, wherein each of said plurality of input data sets is obtained from a different one of a plurality of injections, each of said plurality of input data sets including a same precursor ion having a first retention time and one or more product ions having a retention time within a predetermined retention time window with respect to said first retention time for said precursor ion;

selecting a first of the input data sets in which an intensity of said precursor ion is a maximum with respect to an intensity of said precursor in others of said plurality of input data sets;

after said selecting selects the first input data set in which the intensity of the precursor ion is the maximum, determining a first set of product ions using the first input data set selected in said selecting, wherein each product ion in the first set is in said first input data set selected by said selecting and has a retention time within said predetermined retention time window with respect to said first retention time; and for each product ion in said first set, determining as a first result which of said plurality of input data sets include said each product ion having a retention time that is within said predetermined retention time window with respect to said first retention time, and determining an intensity sum for said each product ion by summing intensities of said each product ion across input data sets in said first result whereby each of said intensities of said each product ion that is summed is an intensity of said each product ion in a different one of the plurality of input data sets included in the first result, wherein said first set of product ions are related to said precursor and each of said product ions in said first set has an intensity sum as determined by said step of determining an intensity sum.

24. A non-transitory computer readable medium comprising executable code stored thereon for matching a precursor ion with one or more related product ions, the non-transitory computer readable medium comprising executable code for:

providing a plurality of input data sets obtained from a plurality of injections, each of said plurality of input data sets including a same precursor ion having a first retention time and one or more product ions having a retention time within a predetermined retention time window with respect to said first retention time for said precursor ion;

determining a first set of product ions, wherein said determining a first set of product ions includes performing a set union operation with respect to product ions included in said plurality of input data sets whereby each product ion in said first set has a retention time within said predetermined retention time window with respect to said first retention time in any of said plurality of input data sets, each product ion in said first set having an intensity that is a sum of intensities of said product ion across input data sets in said plurality which include said each product ion, and in which said each product ion has a retention time within said predetermined retention time window with respect to said first retention time;

selecting a first of the input data sets in which an intensity of said precursor ion is a maximum with respect to an intensity of said precursor in others of said plurality of input data sets;

determining a second set of product ions wherein each product ion in said second set is included in said first input data set selected by said selecting and has a retention time within said predetermined retention time window with respect to said first retention time; and removing product ions from said first set which are not included in said second set, wherein, after performing said removing, said first set includes product ions related to said precursor.

* * * * *